(12) United States Patent
Matsumura

(10) Patent No.: US 8,353,831 B2
(45) Date of Patent: Jan. 15, 2013

(54) DIAGNOSTIC ULTRASOUND SYSTEM AND METHOD OF DISPLAYING ELASTICITY IMAGE

(75) Inventor: Takeshi Matsumura, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 946 days.

(21) Appl. No.: 11/630,164

(22) PCT Filed: Jun. 17, 2005

(86) PCT No.: PCT/JP2005/011109
§ 371 (c)(1),
(2), (4) Date: Dec. 20, 2006

(87) PCT Pub. No.: WO2005/122907
PCT Pub. Date: Dec. 29, 2005

(65) Prior Publication Data
US 2007/0244390 A1 Oct. 18, 2007

(30) Foreign Application Priority Data
Jun. 22, 2004 (JP) .................. 2004-184142

(51) Int. Cl.
*A61B 5/00* (2006.01)
(52) U.S. Cl. ........................................ 600/437
(58) Field of Classification Search .................. 382/128, 382/131; 600/437, 438, 442, 459
See application file for complete search history.

(56) References Cited

U.S. PATENT DOCUMENTS

| | | | |
|---|---|---|---|
| 5,855,557 A * | 1/1999 | Lazenby ................ | 600/443 |
| 6,500,119 B1 * | 12/2002 | West et al. ............ | 600/437 |
| 6,558,324 B1 * | 5/2003 | Von Behren et al. ...... | 600/440 |
| 6,749,571 B2 * | 6/2004 | Varghese et al. ......... | 600/450 |
| 7,303,530 B2 * | 12/2007 | Barnes et al. ........... | 600/459 |
| 2002/0068870 A1 | 6/2002 | Alam et al. | |
| 2002/0095087 A1 * | 7/2002 | Mourad et al. .......... | 600/442 |
| 2005/0090742 A1 * | 4/2005 | Mine et al. ............. | 600/443 |
| 2005/0113691 A1 * | 5/2005 | Liebschner ............. | 600/437 |
| 2008/0221484 A1 * | 9/2008 | Sarvazyan et al. ........ | 600/587 |
| 2008/0287792 A1 * | 11/2008 | Bae et al. .............. | 600/438 |

FOREIGN PATENT DOCUMENTS

| | | |
|---|---|---|
| JP | 2003-225239 | 8/2003 |
| JP | 2004-089362 | 3/2004 |
| JP | 2004-351062 | 12/2004 |

OTHER PUBLICATIONS

Japanese Office Action, dated Feb. 22, 2011, issued in corresponding Japanese Patent Application No. JP 2006-514793.

* cited by examiner

*Primary Examiner* — Tse Chen
*Assistant Examiner* — Rochelle Reardon
(74) *Attorney, Agent, or Firm* — Antonelli, Terry, Stout & Kraus, LLP.

(57) ABSTRACT

A diagnostic ultrasound system includes an ultrasound transmitting and receiving system for transmitting and receiving ultrasonic waves to and from a object to be examined 10, an elasticity image capturing system for capturing an elasticity image related to body tissue of the object to be examined on the basis of a signal output from the ultrasound transmitting and receiving system, and a controlling and displaying system for capturing the elasticity image. The elasticity image capturing system obtains compression data related to the compression state of the object to be examined 10, determines the compression state of the body tissue on the basis of the compression data, and includes a compression direction and range evaluation unit 115 as a compression state evaluating means for reflecting the determination result to the elasticity image. In this way, more accurate diagnosis by objectively and quantitatively grasping the compression state of the body tissue is possible.

28 Claims, 20 Drawing Sheets

FIG. 2
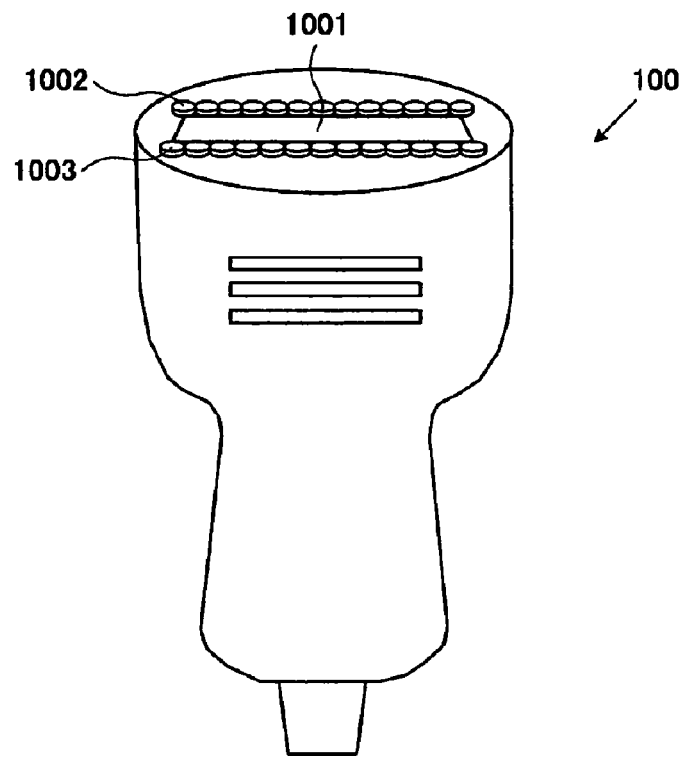
(A)
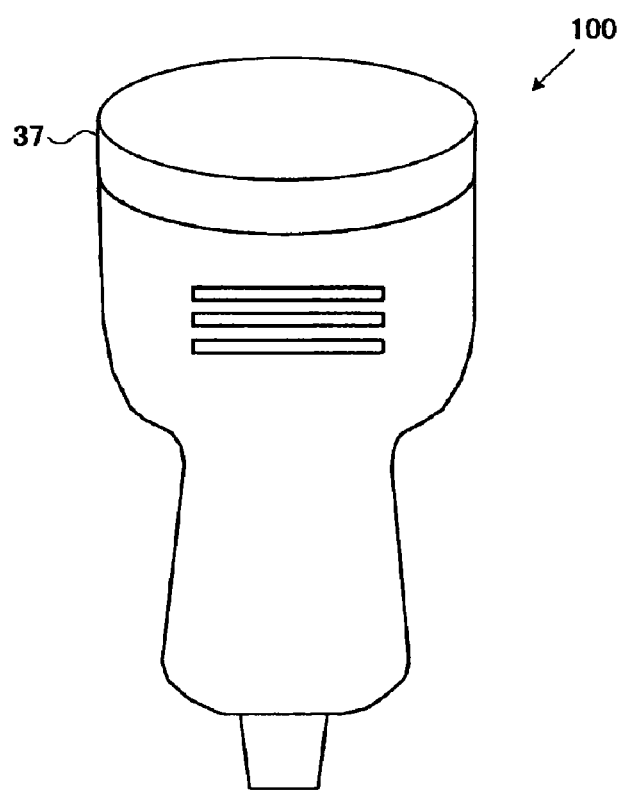
(B)

FIG. 7
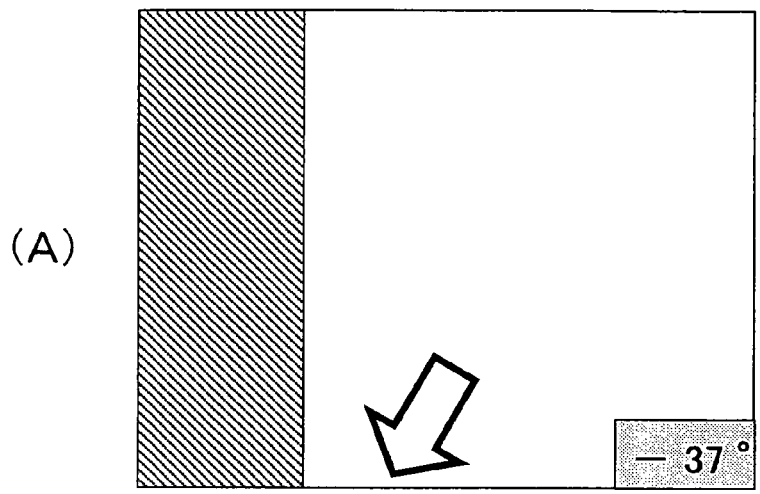
(A)
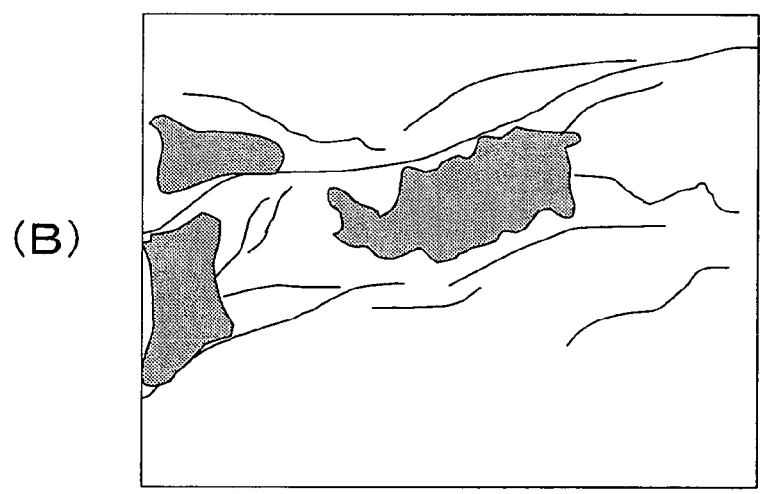
(B)
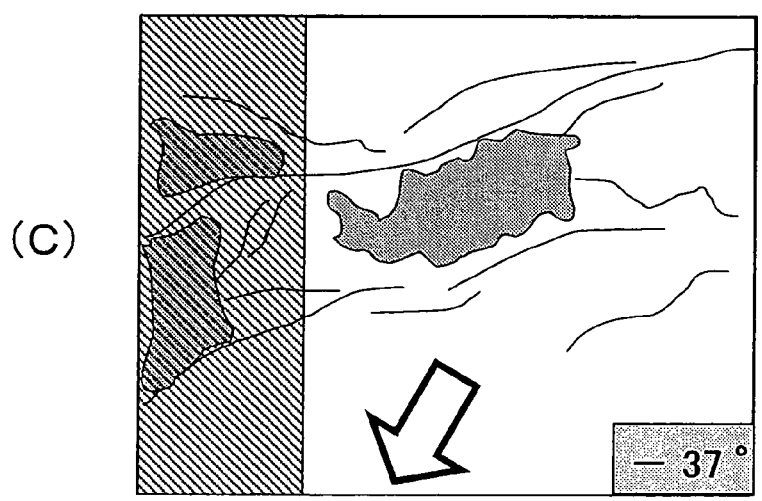
(C)

FIG. 8
(A)
(B)
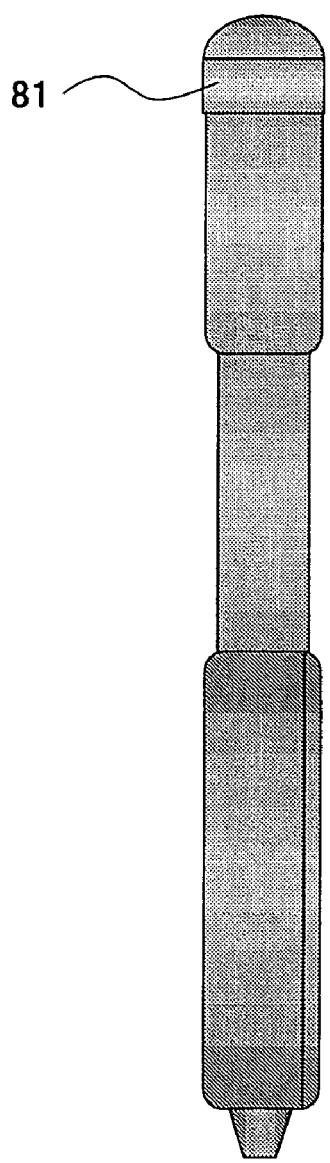
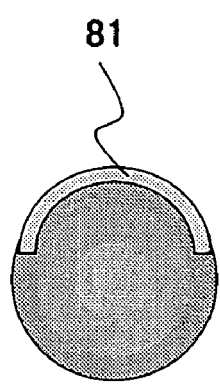

DIAGNOSTIC ULTRASOUND SYSTEM AND METHOD OF DISPLAYING ELASTICITY IMAGE

TECHNICAL FIELD

The present invention relates to a diagnostic ultrasound system for displaying an elasticity image representing the hardness or softness of living tissue of a object to be examined.

BACKGROUND ART

A diagnostic ultrasound system for capturing an ultrasound image of a object to be examined supplies a driving signal for transmission to an ultrasound transducer, emits an ultrasonic wave to the object to be examined, and reconstructs and displays an ultrasound image on the basis of the signal received at the ultrasound transducer.

As such a diagnostic ultrasound system, there is one that displays an elasticity image representing the hardness or softness of living tissue of a object to be examined. For example, an examiner manually compresses an ultrasound transducer whose ultrasound transmission and reception surface is in contact with the object to be examined against the object to be examined. The diagnostic ultrasound system obtains time-sequential images related to the living tissue when pressure is applied to the object to be examined. Elasticity data related to the living tissue is computed in correlation with the obtained time-sequential images, and an elasticity image is constructed on the basis of the computed elasticity data and is displayed.

More specifically, pressure sensors are provided on the back of a transducer element unit of the ultrasound transducer; the pressure applied to the ultrasound transducer by compressing the object to be examined is determined; and Young's modulus is determined to display an elasticity image. When a predetermined threshold of pressure is exceeded, a light emitting diode provided on the ultrasound transducer is emitted. Such a calculation method is described in Patent Document JP2003-225239A.

However, in the Patent Document, only Young's modulus is calculated by determining the pressure applied to the ultrasound transducer, and there is no mentioning of displaying the compression state on a screen. The operation of the ultrasound transducer to compress the object to be examined is carried out manually by the examiner. Therefore, when compressing the object to be examined, the compression direction may deviate from a predetermined direction due to tilting of the ultrasound transmission and reception surface. As a result, pressure may not be uniformly applied to the object to be examined. In other words, a non-uniform stress distribution may be generated in the living tissue of the object to be examined.

As an ultrasound transducer, for example, there is one whose ultrasound transmission and reception surface is curbed toward the living tissue side. When compression operation is carried out with such an ultrasound transmission and reception surface, the pressure in the compression direction may become the greatest because of the shape of the ultrasound transmission and reception surface. In other words, a non-uniform stress distribution may be generated in the living tissue of the object to be examined.

When a non-uniform stress distribution is generated in the living tissue, regions that are sufficiently compressed with predetermined pressure (hereinafter referred to as 'adequate compression ranges') and regions that are insufficiently compressed (hereinafter referred to as 'inadequate compression ranges') both exist in the living tissue in the visual field of the ultrasound transducer. When an elasticity image related to such living tissue is displayed, it is difficult to determined, for example, whether an image corresponding to an inadequate compression range is caused by non-uniformity of the stress distribution or caused by the hardness of the living tissue. Thus, an image corresponding to an inadequate compression range should not be referred to as diagnostic information. However, the process of identifying an adequate compression range and an inadequate compression range in a displayed image depends on the examiner's experience. For this reason, there is a demand for being able to objectively and quantitatively grasping a compression state of living tissue, such as the adequate compression range, the compression direction, and the compression angle.

DISCLOSURE OF INVENTION

An object of the present invention is to provide a diagnostic ultrasound system and a method of displaying an elasticity image capable of a more accurate diagnosis by objectively and quantitatively grasping the compression state of body tissue.

To achieve the above-described object, the diagnostic ultrasound system according to the present invention includes an ultrasound transducer for transmitting and receiving ultrasonic waves to and from a object to be examined; transmitting means for supplying a driving signal to the ultrasound transducer;

receiving means for processing a reception signal output from the ultrasound transducer; elasticity image imaging means for obtaining an elasticity image related to body tissue of the object to be examined on the basis of a signal output from the receiving means; and displaying means for displaying the elasticity image, wherein the elasticity image imaging means includes compression state evaluating means for obtaining compression data related to a compression state of the body tissue of the object to be examined, determining the compression state of the body tissue on the basis of the compression data, and reflecting the determination result on the elasticity image.

In other words, the compression data corresponds to stress generated in the body tissue. Therefore, the determination result based on the compression data can be used as an objective determination index for grasping the compression state (for example, the adequate compression range or the compression direction) of the body tissue. By reflecting the determination result on an elasticity image, the elasticity image can be used to objectively and quantitatively identify the adequate compression range or the compression direction. By visually confirming such an elasticity image, examiners can accurately and easily grasp the compression state (for example, the adequate compression range or the compression direction) on a displayed image, regardless of their experience.

In such a case, the compression state evaluating means can determine an adequate compression range of the body tissue on the basis of a result of comparing the magnitude of the compression data and a set value.

The compression state evaluating means can determine the compression direction of the body tissue on the basis of a distribution of the magnitudes of the compression data at a measurement points in the body tissue.

The compression state evaluating means can obtain elasticity data related to the body tissue and determined at the elasticity image imaging means as the compression data.

The compression state evaluating means can obtain detection values of a plurality of pressure sensors aligned on an ultrasound transmission and reception surface of the ultrasound transducer as the compression data.

A plurality of the pressure sensors that is aligned in a long axis direction of the ultrasound transmission and reception surface may be employed.

A reference deforming body deformable by compression may be employed as pressure sensors.

The compression state evaluating means may obtain a deformation value of the reference deforming body stacked on the ultrasound transmission and reception surface of the ultrasound transducer as the compression data.

The compression state evaluating means may obtain a detection value of a position sensor attached to the ultrasound transducer as the compression data.

The compression state evaluating means may separate elasticity data of measurement points of the body tissue determined at the elasticity image imaging means into displacement vector components of a longitudinal direction corresponding to the depth direction of the object to be examined and a displacement vector components of a lateral direction orthogonal to the depth direction and may determine the adequate compression range by comparing the magnitude of the displacement vector components of the longitudinal direction or the magnitude of the displacement vector components of the lateral direction with a set value.

The compression state evaluating means may separate elasticity data of the measurement points of the body tissue determined at the elasticity image imaging means into displacement vector components of a longitudinal direction corresponding to the depth direction of the object to be examined and a displacement vector components of a lateral direction orthogonal to the depth direction and may determine the compression direction on the basis of the distribution of the magnitude of the displacement vector components of the longitudinal direction or the distribution of the magnitude of the displacement vector components of the lateral direction.

The compression state evaluating means constitutes image data representing the adequate compression range, and the displaying means may display the image data in an superimposing manner on or adjacent to the elasticity image.

The compression state evaluating means constitutes image data or numerical data representing the compression direction, and the displaying means may display the image data or the numerical data in a superimposing manner on or adjacent to the elasticity image.

The compression state evaluating means constitutes image data representing the border of the adequate compression range and an inadequate compression range, and the displaying means may display the image data in an superimposing manner on or adjacent to the elasticity image.

The displaying means may display a region of interest whose size is changed on the basis of a determination result of the compression state evaluating means.

The compression state evaluating means repeatedly determines the adequate compression range in set intervals, and the displaying means may update and display image data representing the adequate compression range in real-time every time the determination result is updated.

The compression state evaluating means repeatedly determines the compression direction in set intervals, and the displaying means may update and display image data or numerical data representing the compression direction in real-time every time the determination result is updated.

The compression state evaluating means constitutes image data of an arrow indicating the compression direction or numerical data representing an angle corresponding to the compression direction, and the displaying means may display an image corresponding to the image data or the numerical data in a superimposing manner on or adjacent to the elasticity image.

The compression state evaluating means repeatedly determines the compression direction in set intervals, and the displaying means may display the time transition of an angle representing the compression direction on the basis of the determination result.

A cine memory for exacting and reading out at least one of the elasticity image stored in advance and image data or numerical data corresponding to the compression state on the basis of compression state evaluation data output from the compression state evaluation unit may be provided.

The compression state evaluating means repeatedly determines the compression direction in set intervals, and the displaying means may display the elasticity image for when an angle representing the compression direction is included in a set range with reference to zero.

The compression state evaluating means repeatedly determines the compression direction in set intervals, and the displaying means time-sequentially may display the elasticity image group for when an angle representing the compression direction is included in a set range with reference to zero.

The compression state evaluating means may include announcing means for generating an alert of at least one of an image and audio when the adequate compression range corresponding to outside a set range.

The compression state evaluating means may include announcing means for generating an alert of at least one of an image and audio when the compression direction corresponding to outside a set range.

A method of displaying an elasticity image according to the present invention includes a transmission and reception step of processing a reception signal output from an ultrasound transducer for alternately converting ultrasonic waves and electric signals after a driving signal for transmission is supplied to the ultrasound transducer; determination step for obtaining compression data related to a compression state of body tissue of a object to be examined on the basis of the reception signal output in the transmission and reception step and determining the compression state of the body tissue on the basis of the compression data; and a display step for displaying the elasticity image reflecting the determination result. In the determination step, a compression range or a compression direction of the body tissue is determined as the compression state.

BRIEF DESCRIPTION OF THE DRAWINGS

FIG. 2 illustrates an example of an ultrasound transducer configured to obtain pressure information.

FIG. 7 illustrates an operation example of a switching adder for constructing display image data by combining an elasticity image, a cross-sectional image, and a compression direction and range image.

FIG. 8 illustrates the exterior of a transrectal probe.

BEST MODE FOR CARRYING OUT THE INVENTION

Figure 1:
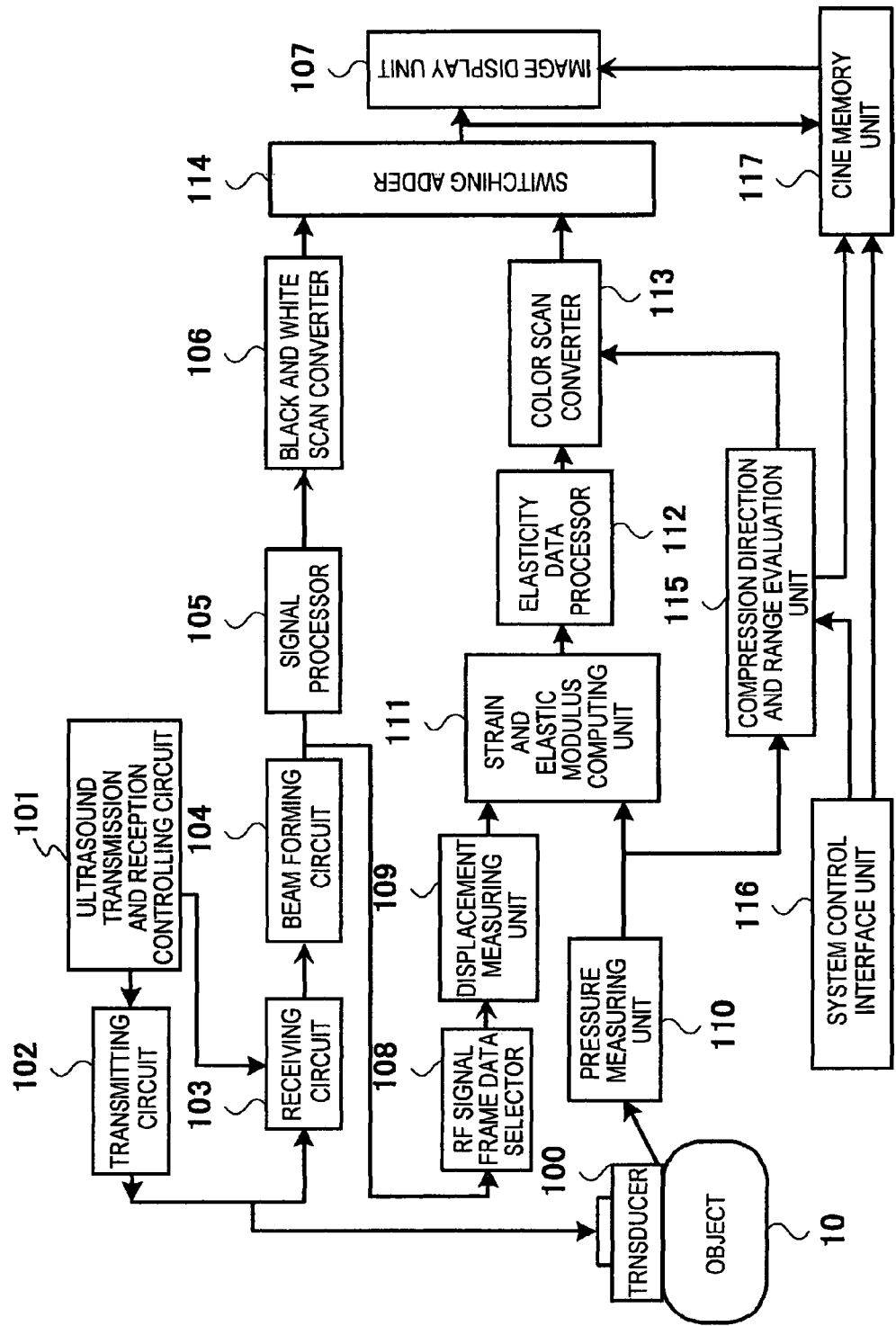
FIG. 1 is a block diagram illustrating the configuration of a diagnostic ultrasound system according to an embodiment of the present invention.

A first embodiment of a diagnostic ultrasound system and a method of displaying an elasticity image employing the present invention will be described with reference to the drawings. FIG. 1 is a block diagram illustrating the configuration of the diagnostic ultrasound system according to this embodiment. The diagnostic ultrasound system captures a cross-sectional image of a region to be diagnosed of a object to be examined 10 by transmitting and receiving ultrasonic waves to and from the object to be examined 10 and captures an elasticity image representing the hardness or softness of living tissue of the region to be diagnosed.

As shown in FIG. 1, the diagnostic ultrasound system includes an ultrasound transducer 100 (hereinafter referred to as 'probe 100') for transmitting and receiving ultrasonic waves to and from the object to be examined 10, a transmitting circuit 102 that is a transmitting means for supplying a driving signal for transmission to the probe 100, a receiving circuit 103 and a beam forming circuit 104 that are receiving means for processing a reception signal output from the probe 100, elasticity image imaging means for obtaining an elasticity image related to the living tissue of the object to be examined 10 on the basis of a signal output from the beam forming circuit 104, and an image display unit 107 that is displaying means for displaying the elasticity image. Here, the elasticity image imaging means includes an RF signal frame data selector 108, a displacement measuring unit 109, a strain and elastic modulus computing unit 111, and a color scan converter 113.

Here, the diagnostic ultrasound system according to this embodiment includes a compression direction and range evaluation unit 115 that is evaluating means for evaluating the compression state of the living tissue of the object to be examined. The compression direction and range evaluation unit 115 obtains compression data related to the compression state of the living tissue of the object to be examined 10, determines the compression state (for example, the adequate compression range or the compression direction) of the living tissue on the basis of the compression data, and reflects the determination result on to an elasticity image.

According to this embodiment, a range in the body tissue of the object to be examined 10 that is sufficiently compressed with predetermined pressure is referred to as an adequate compression range, whereas a region insufficiently compressed is referred to as an inadequate compression range. The compression direction is the direction the probe 100 whose ultrasound transmission and reception surface is in contact with the object to be examined 10 is manually pressed against the object to be examined 10.

The diagnostic ultrasound system will be described in more detail. The diagnostic ultrasound system is broadly classified into an ultrasound transmitting and receiving system, a cross-sectional image capturing system, an elasticity image capturing system, and a controlling and displaying system. As shown in FIG. 1, the ultrasound transmitting and receiving system includes the probe 100, an ultrasound transmission and reception controlling circuit 101, the transmitting circuit 102, the receiving circuit 103, and the beam forming circuit 104.

As shown in FIG. 2A, the probe 100 includes an ultrasound transmission and reception surface 1001 for transmitting and receiving ultrasonic waves to and from the probe 100 by carrying out mechanical or electronic beam scanning. Element groups of transducers for alternately converting ultrasonic waves and electric signals are aligned on the ultrasound transmission and reception surface 1001. The transducer groups are the source of ultrasonic waves transmitted to the object to be examined 10 and receive reflected echo generated at the object to be examined 10. The probe 100 shown in FIG. 2A is a linear probe whose ultrasound transmission and reception surface 1001 is formed as a flat plane. Instead, however, the probe 100 may be, for example, a convex probe whose ultrasound transmission and reception surface 1001 is curved toward the object to be examined 10 side. In other words, various types of probe, such as a transrectal probe, a transesophageal probe, an intraoperative probe, or an intravascular probe, may be used.

As shown in FIG. 2A, pressure sensor groups 1002 and 1003 are disposed in the vicinity of the ultrasound transmission and reception surface 1001 on the probe 100. For example, a plurality of the pressure sensor groups 1002 and 1003 is aligned and disposed in the long axis direction of the ultrasound transmission and reception surface 1001. More specifically, the pressure sensor group 1002 is disposed along one of the long sides of the ultrasound transmission and reception surface 1001. The pressure sensor group 1003 is disposed along the other long side of the ultrasound transmission and reception surface 1001. However, the configuration is not limited to that shown in FIG. 2A, and, for example, a reference deforming body 37 may be stacked on the probe 100 on the surface on the object to be examined 10 side, as shown in FIG. 2B. Here, the surface on the object to be examined 10 side is the surface including the ultrasound transmission and reception surface 1001 of the probe 100. The main point is that a configuration enabling the measurement of the pressure applied to the object to be examined 10 be employed.

The ultrasound transmission and reception controlling circuit 101 outputs a command for controlling the supply timing of the driving signal for transmission to be supplied to the probe 100 to the transmitting circuit 102. The ultrasound transmission and reception controlling circuit 101 outputs a command for controlling the reception timing of a signal output from the probe 100 to the receiving circuit 103. The transmitting circuit 102 includes a signal generating circuit for generating a high-voltage electric pulse for ultrasound transmission as a driving signal and a transmission beam forming circuit for setting the focus point of the ultrasonic waves transmitted from the probe 100 at a predetermined depth in the object to be examined 10. The receiving circuit 103 includes an amplifying circuit for preliminarily amplifying an electric signal corresponding to the reflected echo received at the probe 100 by a predetermined gain. The beam forming circuit 104 phases and adds the phase of the reception signal output from the receiving circuit 103 and forms an ultrasound reception beam with respect to one or a plurality of focus points.

The cross-sectional image capturing system includes the signal processor 105 and the black and white scan converter 106. The signal processor 105 carries out signal processing, such as gain correction, log compression, detection, edge enhancement, filtering, on the signal output from the beam forming circuit 104. The black and white scan converter 106 converts the signal output from the signal processor 105 into a signal for display. More specifically, the black and white scan converter 106 obtains RF signal frame data output from the signal processor 105 at an ultrasound cycle and converts the obtained signal into a digital signal at an analog-digital converter (A/D converter). Next, the black and white scan converter 106 stores the converted signal as a plurality of consecutive and time-sequential cross-sectional image data sets in a plurality of frame memories. The frame memories are installed in the black and white scan converter 106. The black and white scan converter 106 reads out a cross-sectional data group stored in the frame memories in television synchronization, converts the read out cross-sectional data group into an analog signal, and outputs the analog signal to the switching adder 114. The black and white scan converter 106 is provided with a controller for outputting control commands to the A/D converter and the frame memories.

The elasticity image capturing system deviates from the output side of the ultrasound transmitting and receiving system and is dispose in series with the cross-sectional image capturing system. The elasticity image capturing system includes the RF signal frame data selector 108, the displacement measuring unit 109, the pressure measuring unit 110, the strain and elastic modulus computing unit 111, the elasticity data processor 112, the color scan converter 113, and the compression direction and range evaluation unit 115.

The RF signal frame data selector 108 selects, for example, a pair of RF signal frame data sets from the sets of RF signal frame data time-sequentially and continuously output from the beam forming circuit 104. For example, the RF signal frame data selector 108 stores, in order in the frame memories, the RF signal frame data sets continuously output from the beam forming circuit 104 at the frame rate of the diagnostic ultrasound system. The frame memories are installed in the RF signal frame data selector 108. Next, the RF signal frame data selector 108 sets the currently stored sets of RF signal frame data included in the sets of RF signal frame data stored in the frame memories and sets the other sets of RF signal frame data stored in the past as RF signal frame data N-1, N-2, N-3, . . . N-M. In accordance with a control command, the RF signal frame data selector 108 selects one set of RF signal frame data from the RF signal frame data N-1, N-2, N-3, . . . N-M as RF signal frame data X and outputs the selected RF signal frame data X together with the RF signal frame data N to the displacement measuring unit 109. In this way, the RF signal frame data selector 108 has a function for selecting and outputting a pair of RF signal frame data sets (N, X). A case in which the output signal from the beam forming circuit 104 is RF signal frame data has been described. Instead, however, the RF signal frame data may be a signal having an I, Q signal format in which RF signals are complex modulation.

As displacement frame data, the displacement measuring unit 109 measures the amount of displacement or a displacement vector (direction and magnitude of displacement) of the body tissue at each measurement point on the cross-sectional image obtained by the cross-sectional image system on the basis of the pair of RF signal frame data sets output from the RF signal frame data selector 108. For example, the displacement measuring unit 109 carries out one-dimensional or two-dimensional correlation processing on the pair of RF signal frame data sets output from the RF signal frame data selector 108 so as to determine the one-dimensional displacement distribution or the two-dimensional displacement distribution ($\Delta L_{i,j}$) as displacement frame data. Then, the displacement measuring unit 109 outputs the displacement frame data to the strain and elastic modulus computing unit 111 and the compression direction and range evaluation unit 115. As methods of measuring the displacement frame data, for example, the block matching method and the gradient method are known. According to the block matching method, an image is divided into, for example, blocks of N×N pixels; a block that is the most similar to the target block in the current frame is retrieved from the previous frame; and predictive coding is carried out by referring to the retrieved block (for example, Japanese Unexamined Patent Application Publication No. 5-317313). However, the method is not limited to the block matching method or the gradient method, and, instead, for example, a method of calculating displacement according to autocorrelation processing in the same regions in two sets of image data may be employed.

The pressure measuring unit 110 measures the pressure applied to the object to be examined 10 through the probe 100 on the basis of signals output from a pressure sensor group 1002 and 1003 of the probe 100. Then, the pressure measuring unit 110 outputs the measured pressure as pressure data ($\Delta P_{i,j}$) to the strain and elastic modulus computing unit 111 and the compression direction and range evaluation unit 115. Instead of this configuration, the pressure measuring unit 110 may take in a deformation value of the reference deforming body 37 of the probe 100 and measure the pressure applied to the object to be examined 10 on the basis of the taken in deformation value (for example, Japanese Unexamined Patent Application Publication Nos. 2005-013283 and 2005-066041).

The strain and elastic modulus computing unit 111 computes the strain amount distribution and the elastic modulus of the body tissue at each measurement point on the cross-sectional image obtained by the cross-sectional capturing system, on the basis of the displacement frame data ($\Delta L_{i,j}$) output from the displacement measuring unit 109 and the pressure data ($\Delta P_{i,j}$) output from the pressure measuring unit 110. The strain amount distribution ($\epsilon_{i,j}$) is calculated by spatially differentiating ($\Delta L_{i,j}/\Delta X$) the displacement frame data ($\Delta L_{i,j}$). Young's modulus $Ym_{i,j}$, which is one type of elastic modulus, is determined by dividing the pressure at each computation point with the amount of strain at the computation point, as represented by Expression 1. The suffix i,j is an index indicating the coordinates of the frame data. The strain and elastic modulus computing unit 111 generates elasticity frame data on the basis of the strain amount distribution and the elastic modulus of each measurement point and outputs the generated elasticity frame data to the elasticity data processor 112. Instead of using the strain and the elastic modulus of the body tissue when generating elasticity frame data, the strain or elastic modulus calculating unit 111 may use another parameter, such as a stiffness parameter β, a compressive elastic modulus coefficient Ep, or an incremental elastic modulus coefficient Einc (for example, Japanese Unexamined Patent Application Publication No. 5-317313).

$$Ym_{i,j}=(\Delta P_{i,j})/(\Delta L_{i,j}/\Delta X) \quad \text{(Expression 1)}$$

(i,j=1, 2, 3, ...)

The elasticity data processor 112 carries out various types of image processing on the elasticity frame data output from the strain and elastic modulus computing unit 111. For example, the elasticity data processor 112 carries out smoothing on the coordinate plane, contrast optimization, and smoothing between the frames in the time axis direction on the elasticity frame data (for example, Japanese Unexamined Patent Application Publication No. 2004-261198). Then, the elasticity data processor 112 outputs the image-processed elasticity frame data to the color scan converter 113.

The color scan converter 113 includes color information conversion means for adding color information (for example, a red color code, a green color code, or a blue color code) to the elasticity frame data output from the elasticity data processor 112. For example, the color scan converter 113 automatically or manually takes in an upper limit value and a lower limit value that define a selection range for gradating the elasticity frame data via the system control interface unit 116. Then, the color scan converter 113 adds color information to the elasticity frame data on the basis of the gradating selection range. More specifically, the color scan converter 113 converts pixel data that corresponds to a region measured to have great strain with respect to the elasticity frame data output from the elasticity data processor 112 into a red color code. In contrast, the color scan converter 113 converts pixel data that corresponds to a region measured to have small strain into a blue color code. Such elasticity image data output from the color scan converter 113 is displayed on the image display unit 107 as an elasticity image, where the region measured to have great strain is displayed in a red color system and the region measured to have small strain is displayed in a blue color system.

Instead of the color scan converter 113, a black and white scan converter may be used. In such a case, the black and white scan converter increases the brightness of the pixel data of the elasticity frame data that corresponds to a region measured to have great strain. In contrast, black and white scan converter decreases the brightness of the pixel data of the elasticity frame data that corresponds to a region measured to have small strain. Elasticity image data output from such a black and white scan converter is displayed as an elasticity image on the image display unit 107, where the region measured to have great strain includes bright pixels and the region measured to have small strain includes dark pixels.

The compression direction and range evaluation unit 115 determines the adequate compression range and the compression direction of the body tissue of the object to be examined 10. First, the compression direction and range evaluation unit 115 obtains compression data related to the compression state of the body tissue of the object to be examined 10. For example, the compression direction and range evaluation unit 115 takes in, as compression data, at least one of displacement frame data output from the displacement measuring unit 109, elasticity frame data output from the strain and elastic modulus computing unit 111, and pressure data output from the pressure measuring unit 110. The compression direction and range evaluation unit 115 may take in the deformation value of the reference deforming body 37 of the probe 100 as the compression data. Next, the compression direction and range evaluation unit 115 determines the adequate compression range of the body tissue on the basis of the result of comparing the magnitude of the compression data and a set value (threshold value). For example, when the magnitude of the compression data at a measurement point is greater than the threshold value, the compression direction and range evaluation unit 115 determines that the body tissue at the measurement point belongs to the adequate compression range. In contrast, when the magnitude of the compression data at a measurement point is smaller than the threshold value, the compression direction and range evaluation unit 115 determines that the body tissue at the measurement point belongs to an inadequate compression range. Furthermore, the compression direction and range evaluation unit 115 determines the compression direction of the body tissue on the basis of the distribution of the magnitudes of the compression data at the measurement points. Then, the compression direction and range evaluation unit 115 configures image data or numerical data corresponding to the adequate compression range and the compression direction. Here, the image data is, for example, a line image representing the border of the adequate compression range and the inadequate compression range and an arrow image indicating the compression direction. The numerical data is angular data representing the compression direction. The compression direction and range evaluation unit 115 outputs such image data or numerical data corresponding to the adequate compression range and the compression direction to the color scan converter 113. In this way, the elasticity image output from the color scan converter 113 reflects the adequate compression range and the compression direction.

Figure 3:
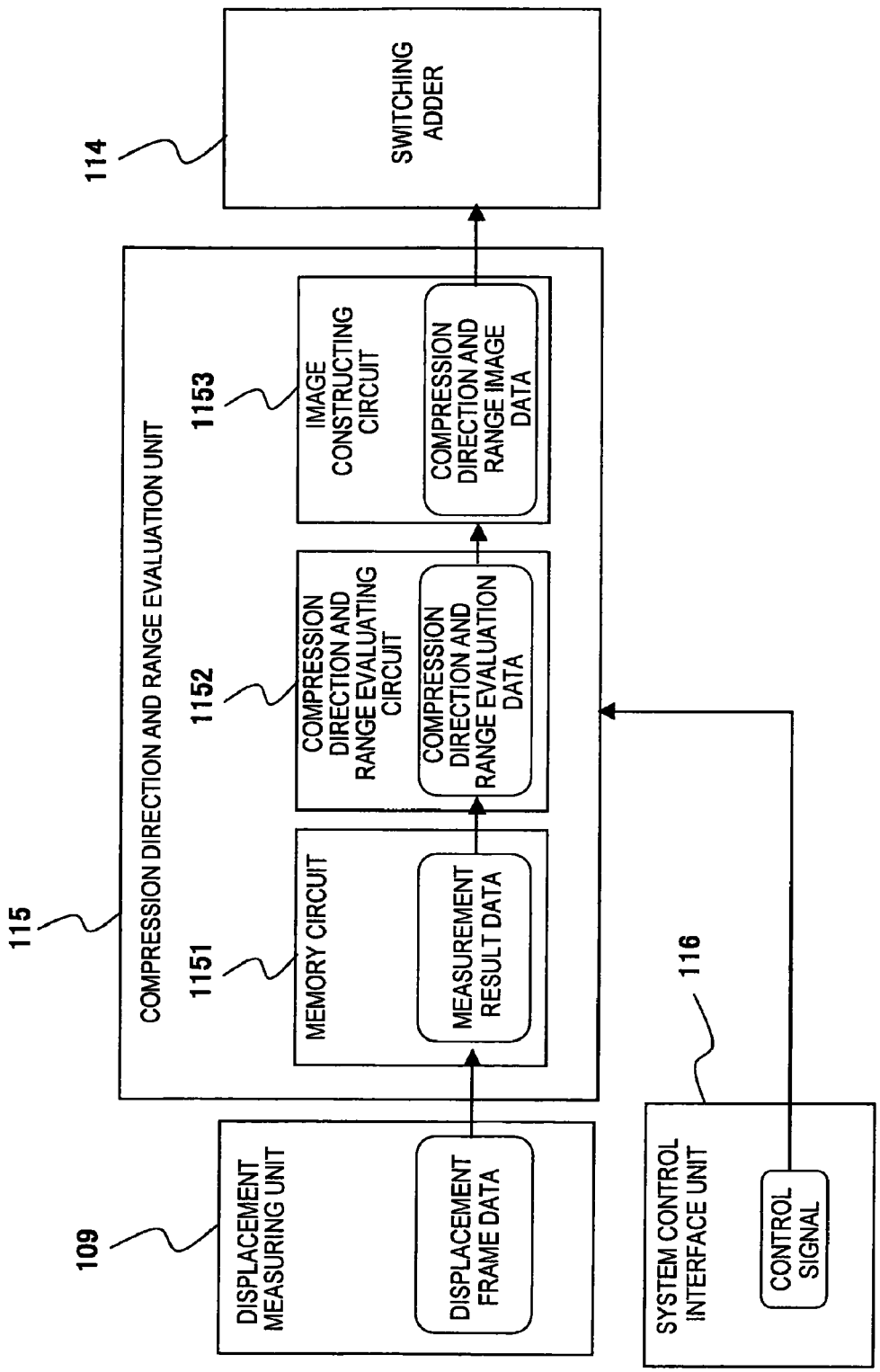
FIG. 3 is a block diagram illustrating a process of a compression direction and range evaluation unit.

FIG. 3 is a block diagram illustrating an embodiment of the compression direction and range evaluation unit 115. As shown in FIG. 3, the compression direction and range evaluation unit 115 includes a memory circuit 1151, a compression direction and range evaluating circuit 1152, and an image constructing circuit 1153. The memory circuit 1151 stores the displacement frame data output from the displacement measuring unit 109 as measurement result data. The compression direction and range evaluating circuit 1152 determines the adequate compression range and the compression direction of the body tissue on the basis of the measurement result data read out from the memory circuit 1151. For example, the compression direction and range evaluating circuit 1152 carries out statistical processing, such as overflow processing and average value calculation, on the measurement result data and outputs the processing result as a determination result to the image constructing circuit 1153. The image constructing circuit 1153 constructs image data or numerical data corresponding to the determination result output from the compression direction and range evaluating circuit 1152. Then, the imaging circuit 1153 outputs the image data or the numerical data to the switching adder 114 via the color scan converter 113.

The controlling and displaying system includes the switching adder 114, the system control interface unit 116, the cine memory unit 117, and the image display unit 107. The switching adder 114 selects or combines the cross-sectional image data output from the black and white scan converter 106 and the elasticity image data output from the color scan converter 113. For example, the switching adder 114 selects and outputs one of the cross-sectional image data and the elasticity image data to the image display unit 107. Alternatively, the switching adder 114 additively combines the cross-sectional image data and the elasticity image data and outputs this to the image display unit 107. When additively combining the cross-sectional image data and the elasticity image data, the switching adder 114 can additively combine the black and white cross-sectional image and the elasticity image in a manner such that the images are displayed in a two-screen display region (for example, Japanese Unexamined Patent Application Publication No. 2000-60853). The switching adder 114 may additively combine the images in a manner such that the elasticity image is translucently overlapped onto the black and white cross-sectional image. Then, the switching adder 114 outputs the selected or additively combined data as display image data to the image display unit 107 and the cine memory unit 117.

The system control interface unit 116 outputs a control command to each component of the diagnostic ultrasound system. The system control interface unit 116 includes inputting means, such as a keyboard and a mouse, and outputs a command input via the inputting means to the compression direction and range evaluation unit 115 and the cine memory unit 117. The cine memory unit 117 stores the display image data output from the switching adder 114 and outputs the display image data to the image display unit 107 in accordance with the control command. The image display unit 107 displays the display image data read out from the switching adder 114 or the display image data read out from the cine memory unit 117 on a display screen.

The basic operation of a diagnostic ultrasound system having the above-described configuration will be described. First, the ultrasound transmitting and receiving system transmits and receives ultrasonic waves to and from the object to be examined 10. For example, the examiner contacts the ultrasound transmission and reception surface side of the probe 100 with, for example, the body surface of the object to be examined 10. After the probe 100 contacts the object to be examined 10, a driving signal for transmission is supplied from the transmitting circuit 102 to the probe 100 at predetermined time intervals in accordance with the command output from the ultrasound transmission and reception controlling circuit 101. In response to the supplied driving signal, ultrasonic waves are repeatedly transmitted from the probe 100 to the object to be examined 10. The transmitted ultrasonic waves are reflected as reflected echo during the process of transmitting through the object to be examined 10. The reflected echo is converted into reception signals by being received in order by the probe 100. The converted reception signals are processed as time-sequential RF signals by the receiving circuit 103 and the beam forming circuit 104.

When ultrasonic waves are transmitted to and received from the object to be examined 10, the examiner manually moves the probe 100 up and down with respect to the body surface of the object to be examined 10. In this way, the pressure applied to the object to be examined 10 is increased or decreased. The pressure applied to the object to be examined 10 is measure by the pressure measuring unit 110 via the pressure sensor groups 1002 and 1003.

The cross-sectional image system configures dark and light cross-sectional image data (for example, black and white cross-sectional image data) of the object to be examined 10. For example, black and white cross-sectional image data is configured by the signal processor 105 and the black and white scan converter 106 on the basis of the time-sequential RF signals output from the beam forming circuit 104.

The elasticity image capturing system configures elasticity image data (for example, color elasticity image data) of the object to be examined 10. For example, displacement frame data related to the amount of movement and displacement of the body tissue corresponding to each measurement point of the cross-sectional image obtained by the cross-section capturing system is determined by the RF signal frame data selector 108 and the displacement measuring unit 109 on the basis of the time-sequential RF signals output from the beam forming circuit 104. Elasticity image data is configured by the strain and elastic modulus computing unit 111, the elasticity data processor 112, and the color scan converter 113 on the basis of the determined displacement frame data and the pressure data output from the pressure measuring unit 110.

An ultrasound image for diagnosis is displayed on a display screen by the controlling and displaying system. For example, the cross-sectional image data output from the black and white scan converter 106 and the elasticity image data output from the color scan converter are selected or additively combined by the switching adder 114 in accordance with a control command. The display image data output from the switching adder 114 is displayed on the image display unit 107. Alternatively, the display image data output from the switching adder 114 is stored in the cine memory unit 117. The stored display image data is read out from the cine memory unit 117 in accordance with a control command. The read out display image data is displayed on the image display unit 107.

Here, an example of the operation of the compression direction and range evaluation unit 115 employed to the diagnostic ultrasound system according to this embodiment will be described in detail. First, an example of evaluating the compression state of the object to be examined 10 with the compression direction and range evaluation unit 115 on the basis of the displacement data output from the displacement measuring unit 109 will be described. More specifically, a method of computing the compression direction and range from the depth direction component of the displacement frame data will be described.

Figure 4:
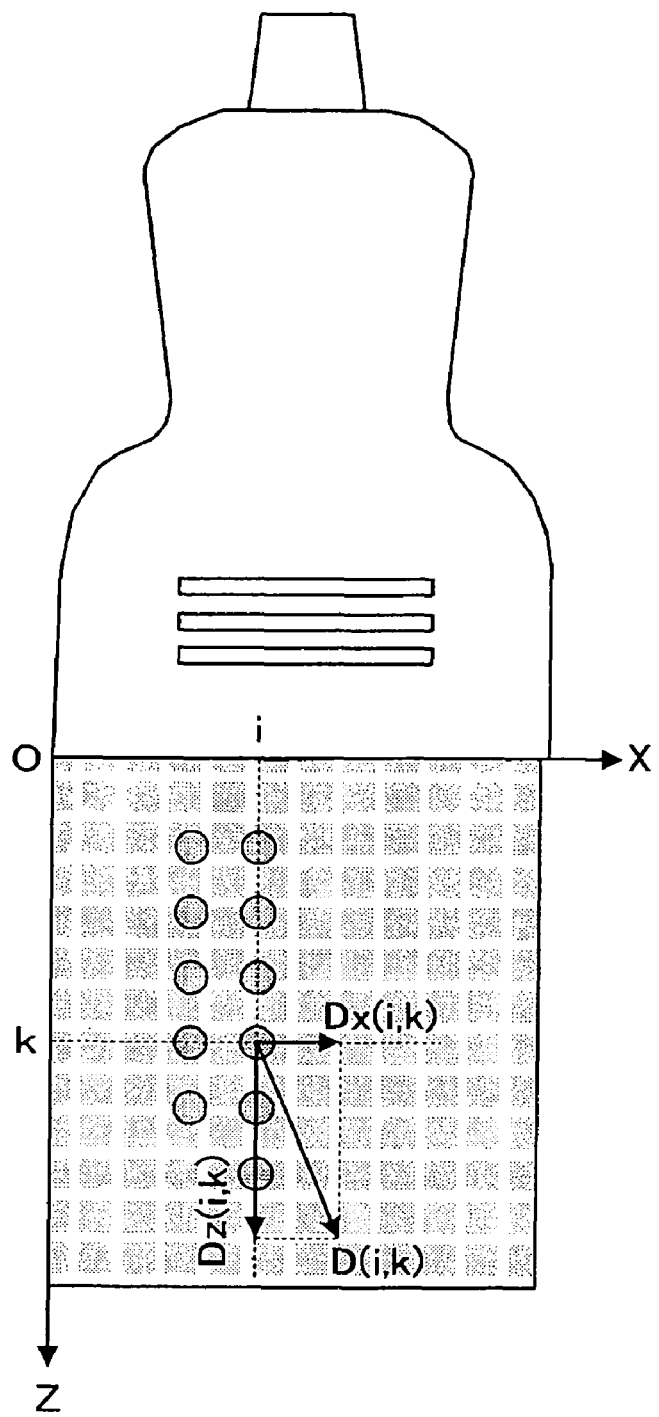
FIG. 4 is a schematic view of a displacement vector, which corresponds to an element of displacement frame data, wherein the displacement vector is separated into a longitudinal direction (depth direction or Z direction) component and a lateral direction (long axis direction of an ultrasound transmission and reception surface of the probe) component.

FIG. 4 schematically illustrates the elements of the displacement frame data as displacement vectors by separating an element into a longitudinal direction component Dz and a lateral direction component Dx. Here, the longitudinal direction (Z direction) corresponds to the depth direction of the object to be examined or, in other words, the emission direction of the ultrasound beam. The lateral direction (X direction) corresponds to a direction orthogonal to the depth direction of the object to be examined or, in other words, the long axis direction of the ultrasound transmission and reception surface. The longitudinal direction component Dx and the lateral direction component Dx shown in FIG. 4 are represented as Expression 2. Index i in Expressions 2 represents the coordinate in the lateral direction. Index k represents the coordinate in the longitudinal direction. By using indices i and k, the entire displacement frame data group is referred to.

$Dx(i,k)$ (i=1, 2, 3, ... L; k=1, 2, 3, ... N)

$Dz(i,k)$ (Expression 2)

(i=1, 2, 3, ... L; k=1, 2, 3, ... N)

The displacement frame data groups Dx(i,k) and Dz(i,k) output from the displacement measuring unit 109 are stored in the memory circuit 1151, shown in FIG. 3, as measurement result data groups Rx(i,k) and Rz(i,k). The stored measurement result data groups Rx(i,k) and Rz(i,k) are represented as Expressions 3.

$Rx(i,k)$ (i=1, 2, 3, ... L; k=1, 2, 3, ... N)

$Rz(i,k)$ (Expression 3)

(i=1, 2, 3, ... L; k=1, 2, 3, ... N)

Figure 5:
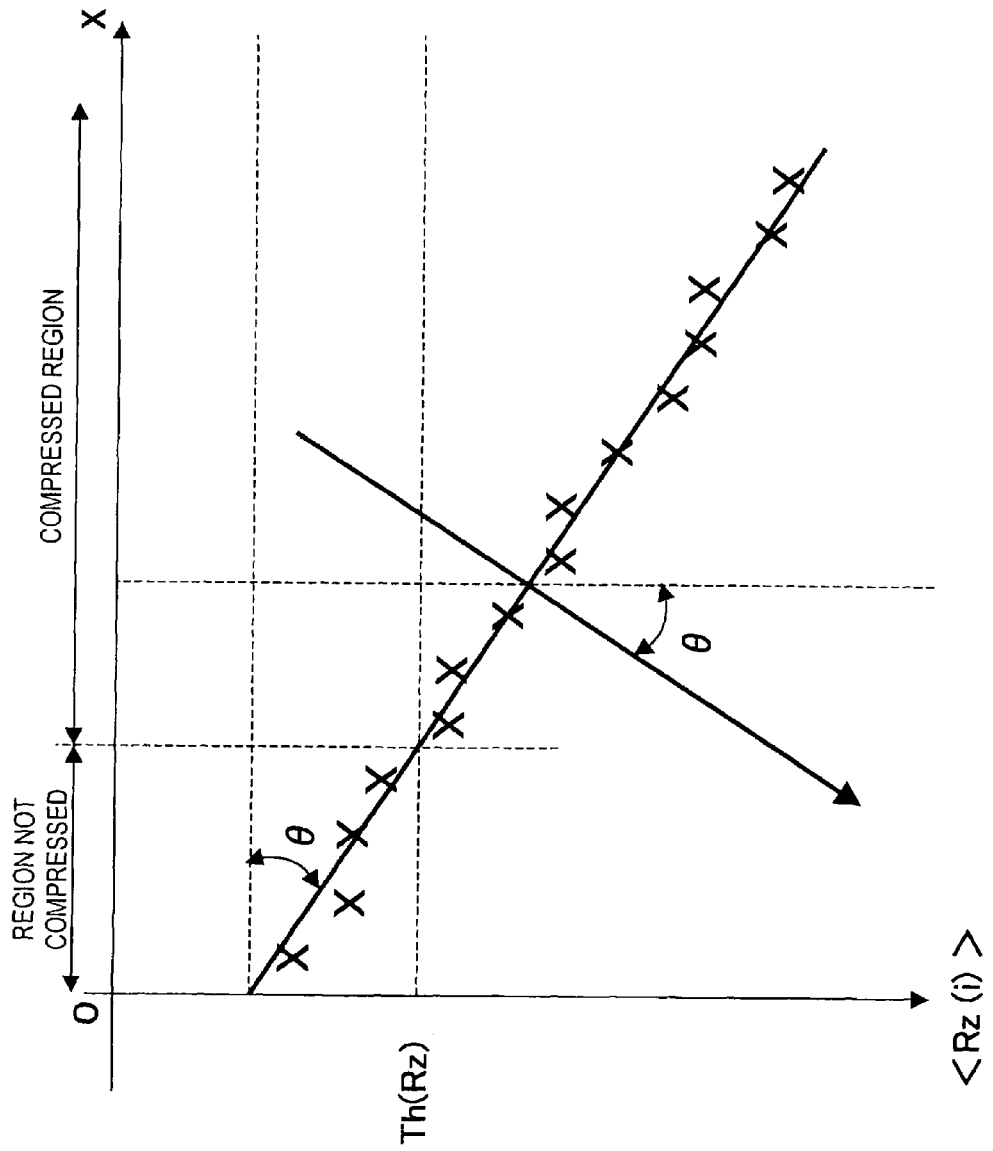
FIG. 5 illustrates a computation example of determining an adequate compression range and an inadequate compression range on the basis of the displacement Rz(i,k) in the longitudinal direction.

Next, as a computation example for determining an adequate compression range and an inadequate compression range of body tissue, a method using the displacement Rz(i,k) in the longitudinal direction will be described with reference to FIG. 5. FIG. 5 is a line graph defining the border of the adequate compression range and the inadequate compression range. The line graph includes an axis corresponding to the longitudinal direction (Z direction) and an axis corresponding to the lateral direction (X direction).

First, the strain and elastic modulus computing unit 111 computes a value obtained by computing the average value of the values of the longitudinal direction displacement among coordinate points in the same lateral direction on the basis of Expression 4. In other words, the strain and elastic modulus computing unit 111 computes the average value of the longitudinal direction displacement for each lateral direction coordinate. Next, the strain and elastic modulus computing unit 111 plots the computed values according to Expression 4 on the graph shown in FIG. 5. Each cross mark shown in FIG. 5 represents the plotted value of <Rz(i)> at each lateral direction coordinate point (i=1, 2, 3, ... L). In the configuration shown in FIG. 5, L equals 15 for the sake of explanation, but the value is not limited. Next, the strain and elastic modulus computing unit 111 determines a straight line by carrying out approximation based on, for example, the least-square method on the computed values plot on the graph shown in FIG. 5.

Then, the strain and elastic modulus computing unit 111 determines that the slope θ of the straight line shown in FIG. 5 is numerical data representing the angle corresponding to the compression direction of the body tissue. When the object to be examined 10 is compressed in the +Z direction or, in other words, pressed with the probe 100, the value of the displacement is set so that it has a positive (+) sign. In contrast, when the object to be examined 10 is decompressed in the −Z direction or, in other words, when the probe 100 is pulled away from the object to be examined 10, the value of the displacement is set so that it has a negative (−) sign. A computation method representing the configuration shown in FIG. 5 has been described. However, the computation process is not limited to when the object to be examined 10 is compressed but can also be employed when the object to be examined 10 is decompressed.

$<Rz(i)>=\{ZkRz(i,k)\}/N$ (Expression 4)

The strain and elastic modulus computing unit 111 determines the adequate compression range on the basis of the line graph shown in FIG. 5. For example, the strain and elastic modulus computing unit 111 sets a threshold value Th(Rz) for the depth direction displacement. The threshold value Th(Rz) is a set value output from the system control interface unit 116 to the compression direction and range evaluation unit 115. For this set value, a minimum value of the depth direction displacement is determined in advance so as to determine a region that corresponds to the adequate compression range. Then, the strain and elastic modulus computing unit 111 determines that the lateral direction coordinate region exceeding the threshold value Th(Rz) as being the adequate compression range and the lateral direction coordinate region not exceeding the threshold value Th(Rz) as being the inadequate compression range. The coordinate region determined to be the adequate compression range is set as Pth(i)=1. The coordinate region determined to be the inadequate compression range is set as Pth(i)=0. For example, in the case of FIG. 5, a coordinate region is set as Expressions 5. The strain and elastic modulus computing unit 111 identifies the border of the region whose Pth(i) value is set to "1" and the region whose Pth(i) value is set to "0" as the border of the adequate compression range and the inadequate compression range. By employing such a method, the strain and elastic modulus computing unit 111 sets the data of the compression angle θ and the compression range Pth(i) as the compression direction and range evaluation data.

$Pth(1 \leq i \leq 4)=0$ $Pth(5 \leq i \leq 15)=1$ (Expressions 5)

Figure 6:
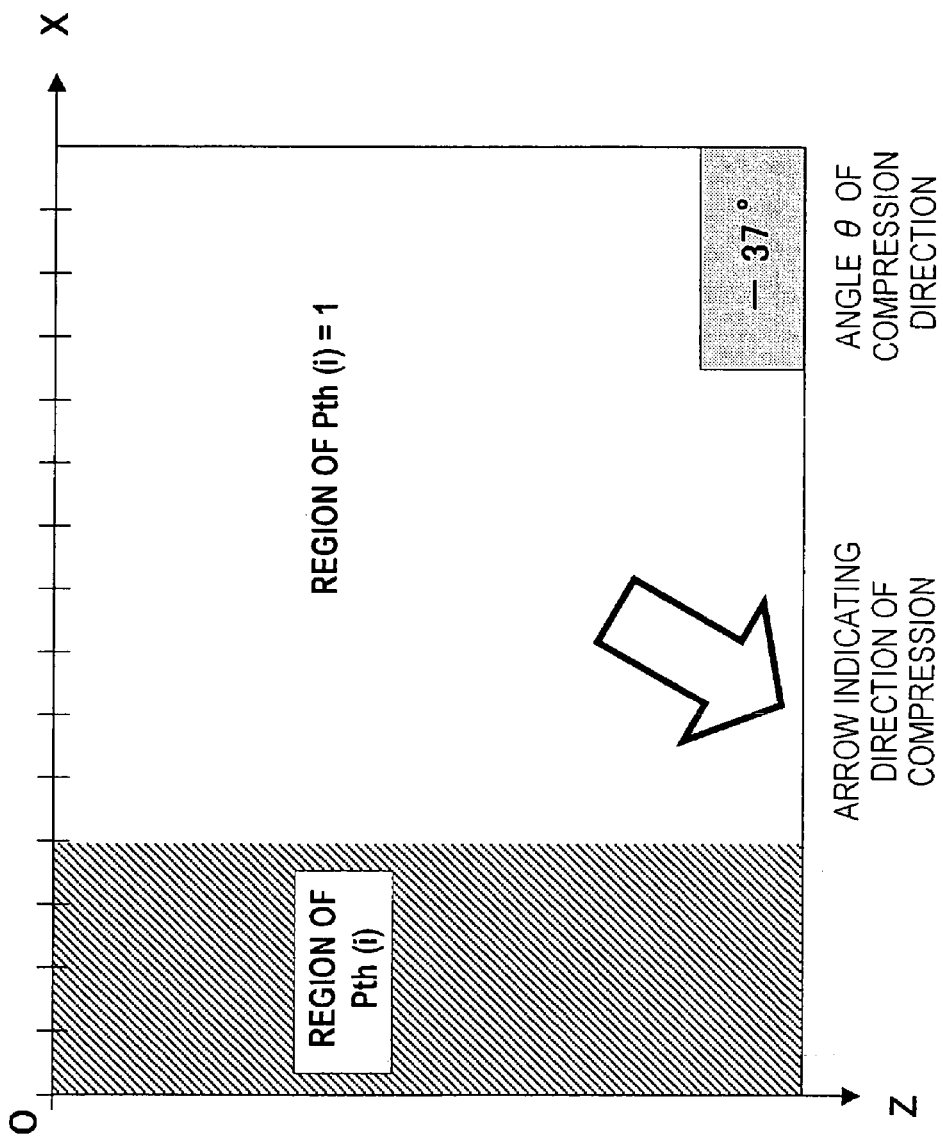
FIG. 6 illustrates an example of compression direction and range image data for displaying the compression direction and range that is constructed by an image constructing circuit.

FIG. 6 illustrates an example of compression direction and range evaluation data constructed by the image constructing circuit 1153, shown in FIG. 3. Here, the compression direction and range evaluation data is data representing the compression direction and the adequate compression range corresponding to the compression direction and range evaluation data. The image constructing circuit 1153 configures, for example, compression direction and range evaluation data corresponding to the values of the compression angle θ and the compression range of Pth(i), as shown in FIG. 6. In the configuration shown in FIG. 6, a white color code is assigned to the pixel points corresponding to the adequate compression range. On the other hand, a black color code is assigned to a predetermined percentage of the pixel points corresponding to the inadequate compression range. Image data for an arrow corresponding to the compression angle θ and pointing in the compression direction is configured. Moreover, the value of the compression angle θ (for example, "−37°") is configured as image data. According to this embodiment, the image and numerical value corresponding to the compression angle θ and the image corresponding to the adequate compression range are simultaneously displayed on the same screen. However, only one of these may be displayed. Such compression direction and range evaluation image data reflects the current compression state. In other words, when the compression direction or the adequate compression range of the body tissue within the region of interest changes, the image constructing circuit 1153 updates the compression direction and range evaluation image data in real-time by following the change.

FIG. 7 illustrates an operation example of the switching adder 114 employed to the diagnostic ultrasound system according to this embodiment. FIG. 7A illustrates the compression direction and range image shown in FIG. 6. FIG. 7B illustrates a combined image that combines a cross-sectional image obtained by the cross-sectional image capturing system and an elasticity image obtained by the elasticity image capturing system. FIG. 7C illustrates a display configuration of the image display unit 107.

The switching adder 114 outputs the compression direction and range evaluation image (FIG. 7A) output from the compression direction and range evaluation unit 115 and the display image data with an superimposing combined image (FIG. 7B) of the cross-sectional image and the elasticity image are output to the image display unit 107. The display image data is displayed on the image display unit 107 as an ultrasound diagnosis image.

According to the method of evaluating a compression state described with reference to FIGS. 4 to 7, the examiner can diagnose the object to be examined more accurately as a result of being able to objectively determining the compression state (for example, the adequate compression range, the compression direction, and the compression direction) of the body tissue in a quantitative quantity on the display screen. In other words, the compression data according to this embodiment corresponds to the stress generated in the body tissue. Therefore, the determination result based on the compression data (for example, displacement frame data) can be an objective index for grasping the adequate compression range or the compression direction of the body tissue. By reflecting this determination result to the elasticity image, the adequate compression range and the compression direction can be objectively and quantitatively identified from the elasticity image. By visually confirming such an elasticity image, the examiner can correctly and easily grasp the adequate compression range or the compression direction on the display screen, regardless of the difference in their experience.

FIG. 8 illustrates a configuration in which a convex probe 100 is employed to the diagnostic ultrasound system instead of the linear probe 100 shown in FIG. 2. FIG. 8A is a side view of the probe 100. FIG. 8B illustrates the probe 100 viewed from the tip. The probe 100 shown in FIG. 8 is used for transrectal examination. As shown in FIG. 8, the probe 100 includes a cylindrical main body and is provided with a head-forming section disposed at the tip of the body. A transducer element group 81 is disposed on the cylindrical surface in the vicinity of the tip of the head-forming section. The circumferential surface of the head-forming section has a relatively large curvature of, for example, 20 mm. In other words, the convex probe 100 is formed such that the ultrasound transmission and reception surface is curved toward the tissue of the object to be examined to be compressed. In a similar manner as the case shown in FIG. 2A, pressure sensor groups 1002 and 1003 are provided around the ultrasound transmission and reception surface. Furthermore, in a similar manner as the case shown in FIG. 2B, a reference deforming body 37 may be attached to the ultrasound transmission and reception surface.

Figure 9:
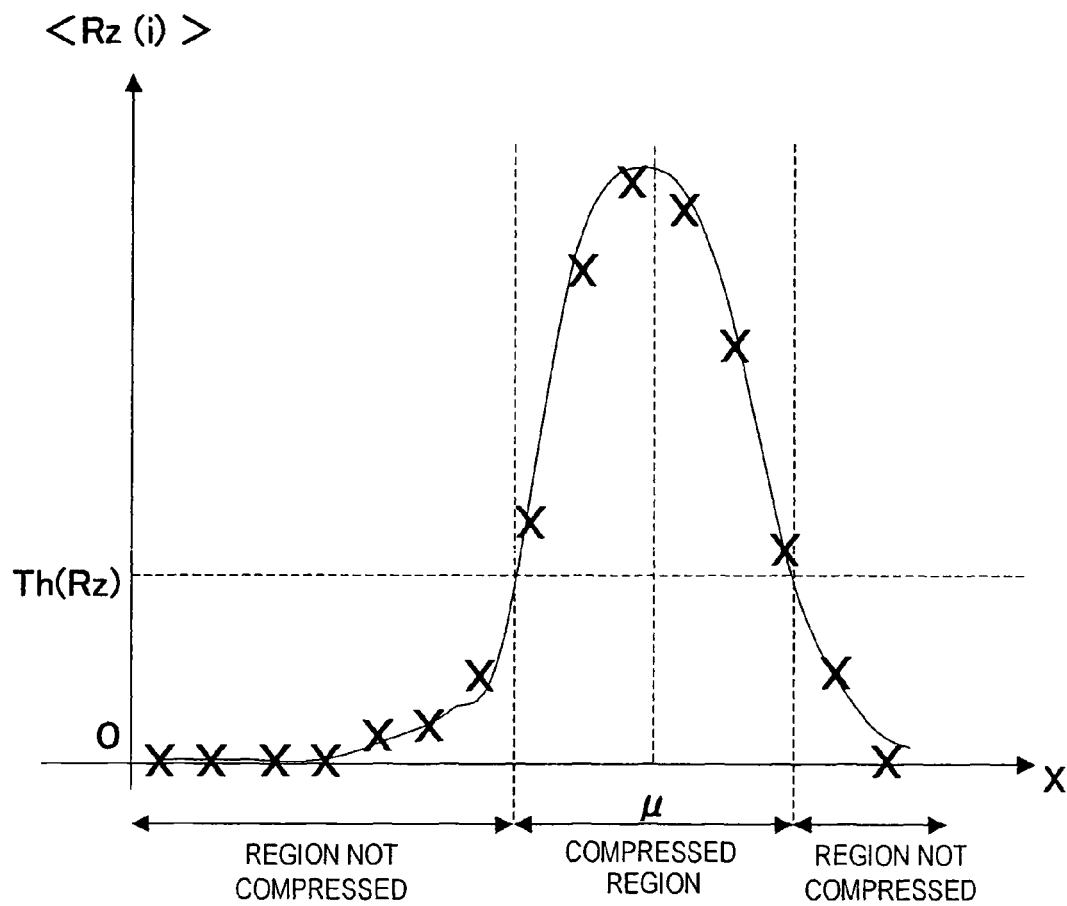
FIG. 9 illustrates a computation example of determining an adequate compression range and an inadequate compression range on the basis of an average value of depth direction displacement.

FIG. 9 illustrates the operation of the compression direction and range evaluation unit 115 when body tissue is compressed with the probe 100 shown in FIG. 8. As shown in FIG. 9, because of the shape of the ultrasound transmission and reception surface of the probe 100, when the probe 100 is misaligned even slightly from the center of the compression direction, the compression direction is the inadequate compression range. Thus, the compression direction and range evaluation unit 115 obtains a curve such as that shown in FIG. 9 by approximating (fitting) the displacement Rz(i) in the depth direction to, for example, a normal distribution function. Next, the compression direction and range evaluation unit 115 determines the average value μ of the approximated normal distribution function as the average value of the depth direction displacement. Then, the compression direction and range evaluation unit 115 determines the radial axis direction at a coordinate of long axis direction X=μ of the ultrasound transmission and reception surface of the probe 100 as the center of the compression direction. In the same manner as the configuration shown in FIG. 5, the compression direction and range evaluation unit 115 sets the threshold value Th(Rz) of the depth displacement and determines the adequate compression range and the inadequate compression range separated by the threshold value Th(Rz).

Figure 10:
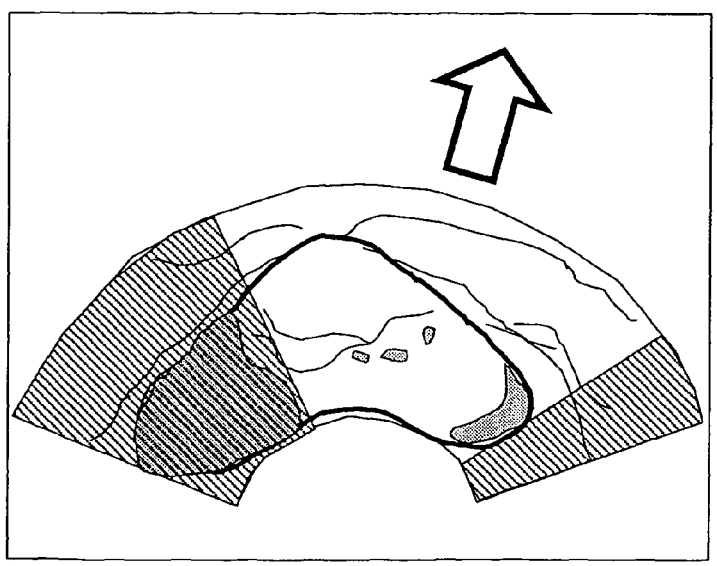
FIG. 10 illustrates an example of a method of configuring display image data by combining an elasticity image, a cross-sectional image, and a compression direction and range image.

FIG. 10 illustrates an example of a displayed image for when the body tissue is compressed with the probe 100 shown in FIG. 8. As shown in FIG. 10, in the fan-shaped displayed image, a white color code is assigned to the pixel points corresponding to the adequate compression range. In contrast, a black code is assigned to a predetermined percentage of the pixel points corresponding to the inadequate compression range. An image of an arrow corresponding to the compression angle θ and pointing in the compression direction is displayed. In this way, for example, when a transrectal probe 100 is used to examine prostate cancer, the body tissue in the inadequate compression range can be prevented from being falsely diagnosed as positive. It is significantly effective to display an objective and quantitative determination index of the compression state (for example, the adequate compression range, the compression direction, and the compression angle) when using a probe 100 configured in a manner shown in FIG. 8.

Figure 11:
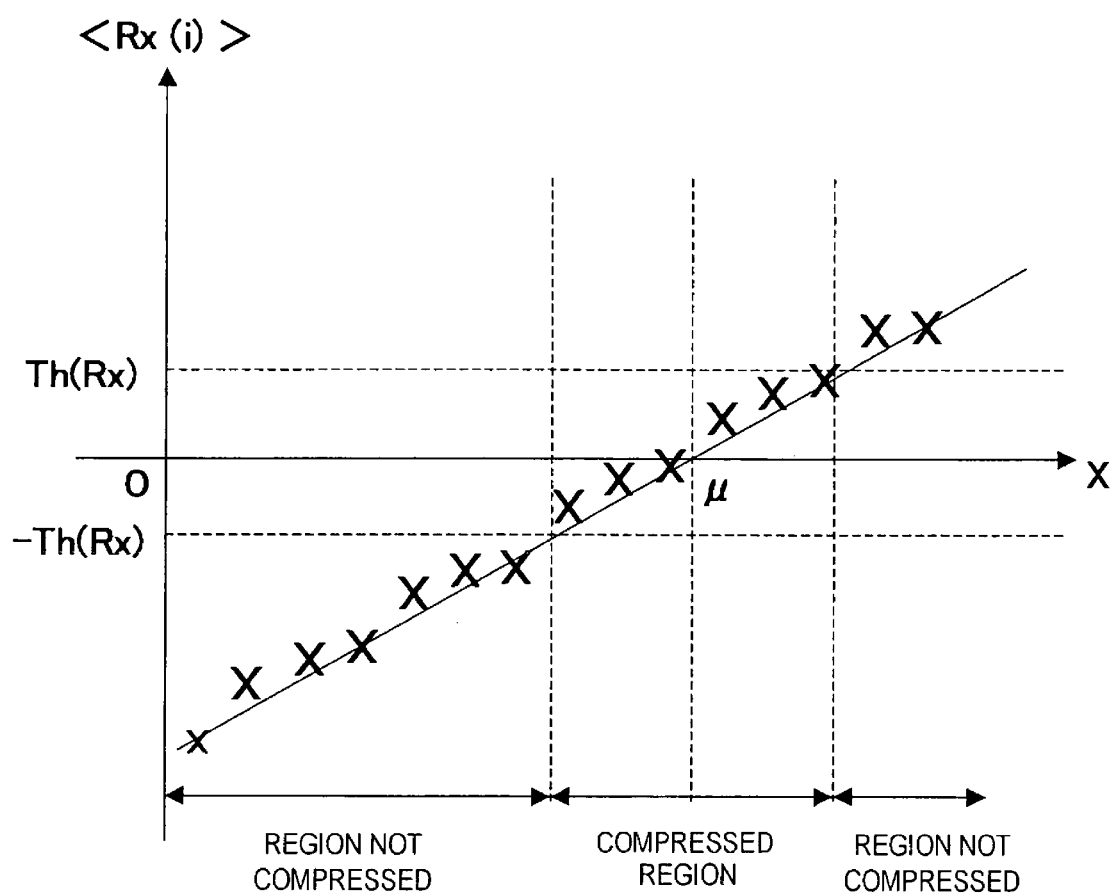
FIG. 11 illustrates a computation example of determining an adequate compression range and an inadequate compression range on the basis of an average value of lateral direction displacement.

FIG. 11 illustrates another example of the computation method described with reference to FIG. 5. The configuration shown in FIG. 11 differs from the configuration that uses displacement frame data of the longitudinal direction shown in FIG. 5, in that displacement frame data of the lateral direction is used. More specifically, according to the configuration shown in FIG. 5, the compression direction and range evaluation unit 115 determines, for example, the compression direction by curve-approximating the displacement distribution in the depth direction (Z direction). In contrast, according to the configuration shown in FIG. 11, the compression direction and range evaluation unit 115 curve-approximates the displacement distribution in the lateral direction (X direction).

For example, the displacement distribution in the lateral direction for when the target tissue is compressed with the convex probe 100 will have a configuration shown in FIG. 11. The cross mark shown in FIG. 11 represents the plotted value of the depth direction average <Rx(i)> of the lateral direction displacement at each lateral direction coordinate point (i=1, 2, 3, . . . L). In this configuration, L equals 15. As shown in FIG. 11, the points whose average value <Rx(i)> is positive correspond to points having a component displaced in the +X direction. The points whose average value <Rx(i)> is negative correspond to points having a component displaced in the −X direction. Here, as shown in the drawing, the compression direction and range evaluation unit 115 approximates the plotted points of the computation result to a straight line by employing, for example, the least-square method. Next, the compression direction and range evaluation unit 115 sets the intersecting point of the approximated straight line and the X axis as µ. Then, the compression direction and range evaluation unit 115 determines that the body tissue group is located at the center or in the vicinity of the center of the compression direction because the body tissue group distributed from the X=µ coordinate in the radial axis direction does not have many displacement components in the lateral direction.

Similar to the configuration shown in FIG. 5, the compression direction and range evaluation unit 115 sets a threshold value Th(Rx) of the lateral direction displacement. Then, the compression direction and range evaluation unit 115 interprets that components diverge to the lateral direction of the body tissue in regions whose lateral direction displacement is greater than Th(Rx) and regions whose lateral direction displacement is smaller than −Th(Rx) and determines these regions as inadequate compression ranges. In other words, the compression direction and range evaluation unit 115 determines regions whose absolute value of the lateral direction displacement is greater than the absolute value of Th(Rx) as inadequate compression ranges.

In the configurations shown in FIG. 5 or 8, the compression direction and range evaluation unit 115 evaluates and estimates the compression state (for example, the adequate compression range, the compression direction, and the compression angle) on the basis of either the longitudinal direction components or the lateral direction components of the displacement vector related to the body tissue. However, the configuration is not limited, and the compression direction and range evaluation unit 115 may evaluate and estimate the compression state on the basis of both the longitudinal direction components and the lateral direction components. In this way, the evaluation accuracy and the estimation accuracy are increased compared with when either the longitudinal direction components or the lateral direction components is used.

In the configurations described with reference to FIGS. 3 to 11, the compression direction and range evaluation unit 115 uses the displacement frame data output from the displacement measuring unit 109 when evaluating or estimating the compression state. However, the configuration is not limited, and the compression direction and range evaluation unit 115 may use numerical value data (elasticity frame data) of the strain or the elastic modulus output from the strain and elastic modulus computing unit 111, instead of the displacement frame data.

Figure 12:
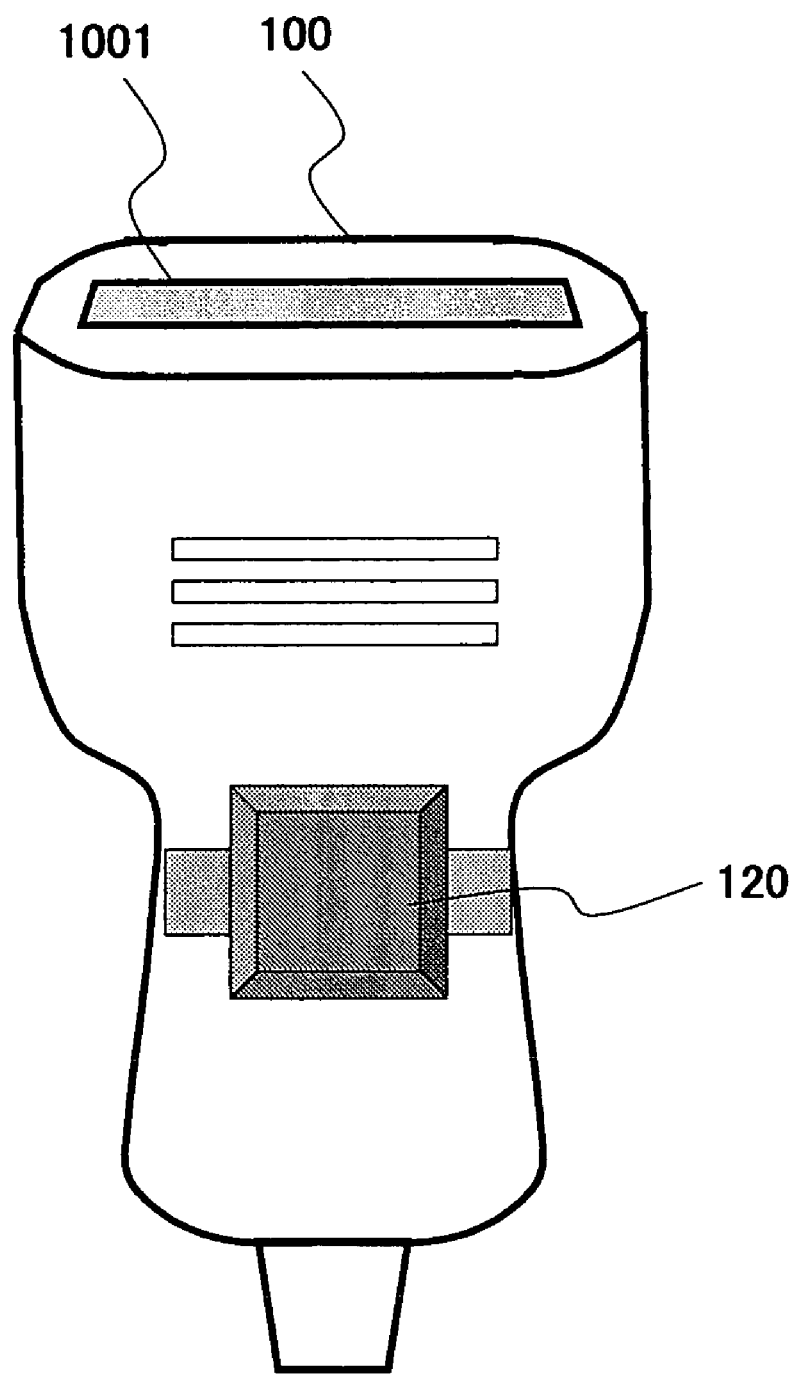
FIG. 12 illustrates an ultrasound transducer provided with a magnetic sensor.
Figure 13:
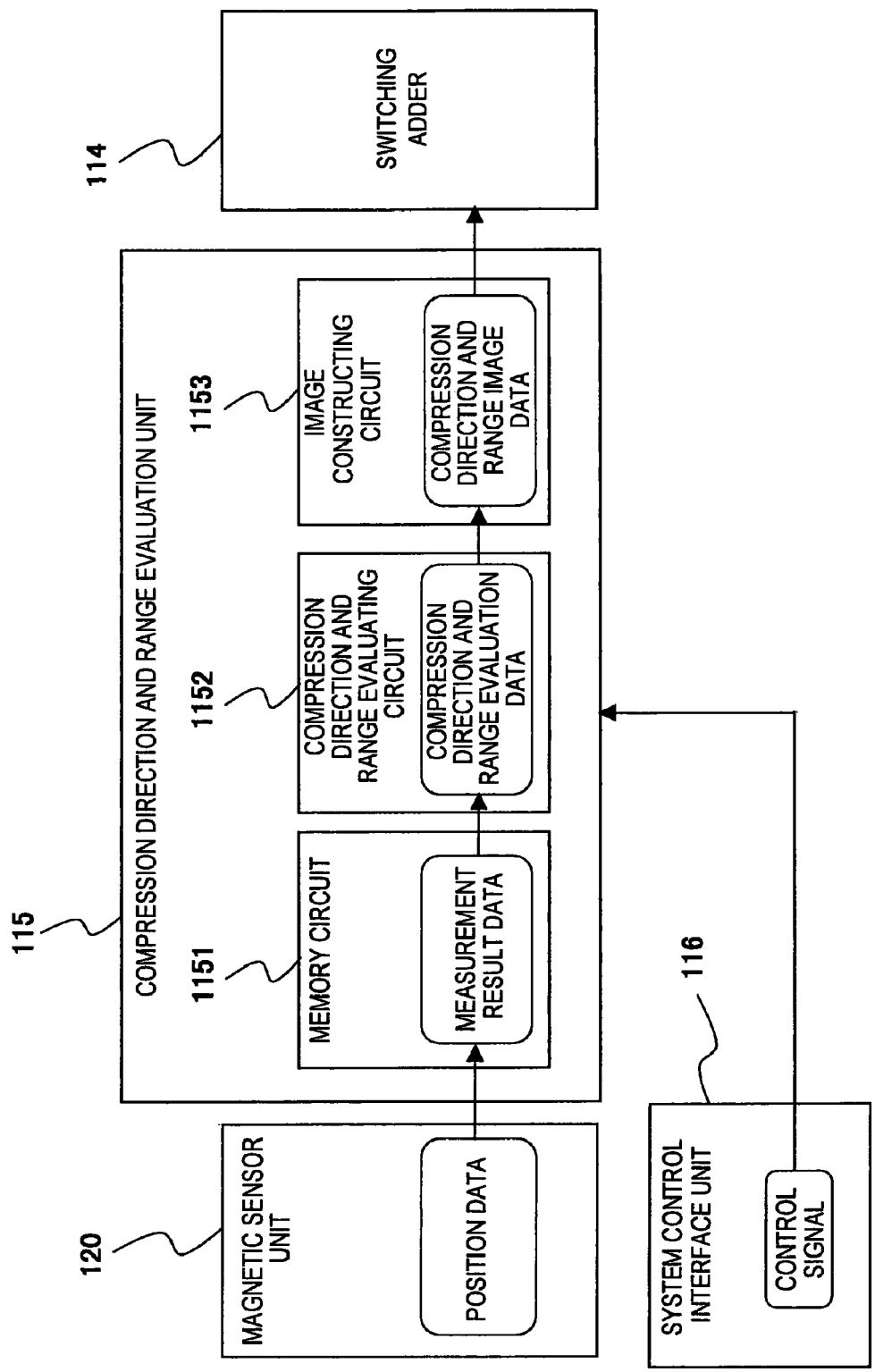
FIG. 13 is a block diagram illustrating an embodiment of a compression direction and range evaluation unit for measuring the compression direction on the basis of position data measured by the magnetic sensor.

The compression direction and range evaluation unit 115 may set a detection value of a position sensor attached to the probe 100 as compression data, instead of the displacement frame data or the elasticity frame data. FIG. 12 illustrates the configuration of the probe 100 provided with a magnetic sensor 120 as a position sensor. FIG. 13 illustrates a configuration in which the magnetic sensor 120 is provided on the input side of the compression direction and range evaluation unit 115. As shown in FIGS. 12 and 13, the magnetic sensor 120 uses magnetism or light to detect the position of the magnetic sensor 120 as position data. Next, the compression direction and range evaluation unit 115 determines the movement direction of the probe 100 on the basis of the position data output from the magnetic sensor 120. Then, the compression direction and range evaluation unit 115 evaluates or estimates the compression direction of the body tissue on the basis of the movement direction of the probe 100. The adequate range of the body tissue may be estimated on the basis of the field range and the compression direction of the probe 100 or on the basis of other methods described above.

Figure 14:
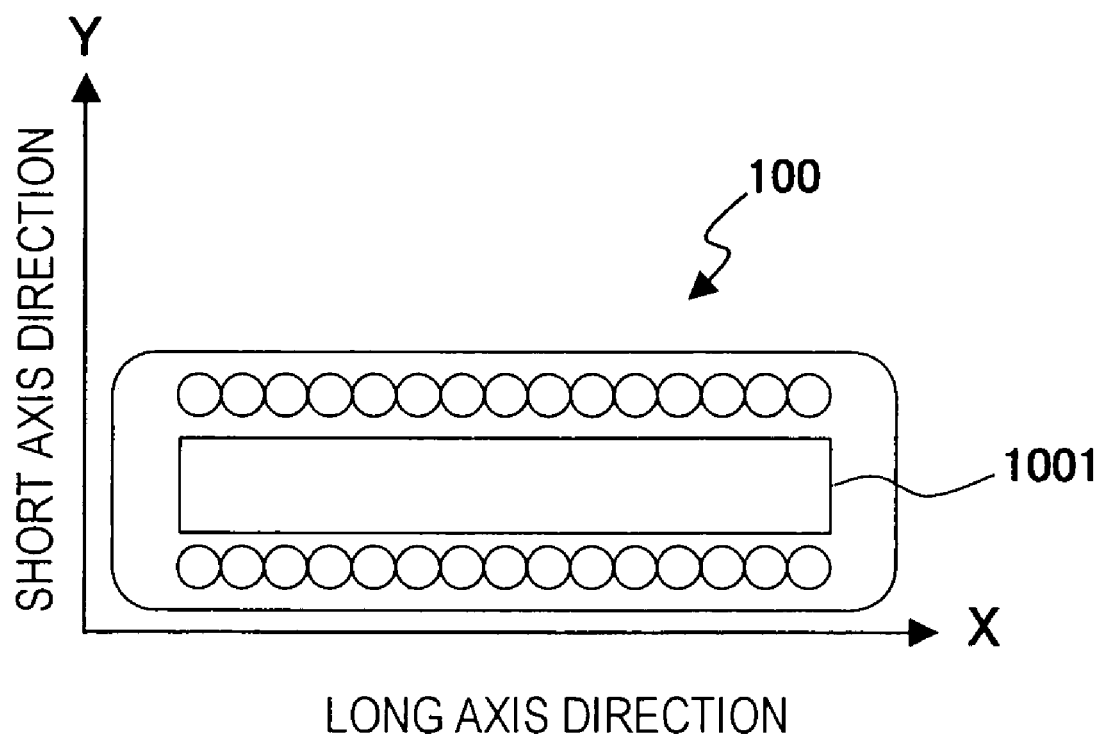
FIG. 14 illustrates an ultrasound transducer provided with a pressure sensor group viewed from the ultrasound transmission and reception surface side.
Figure 15:
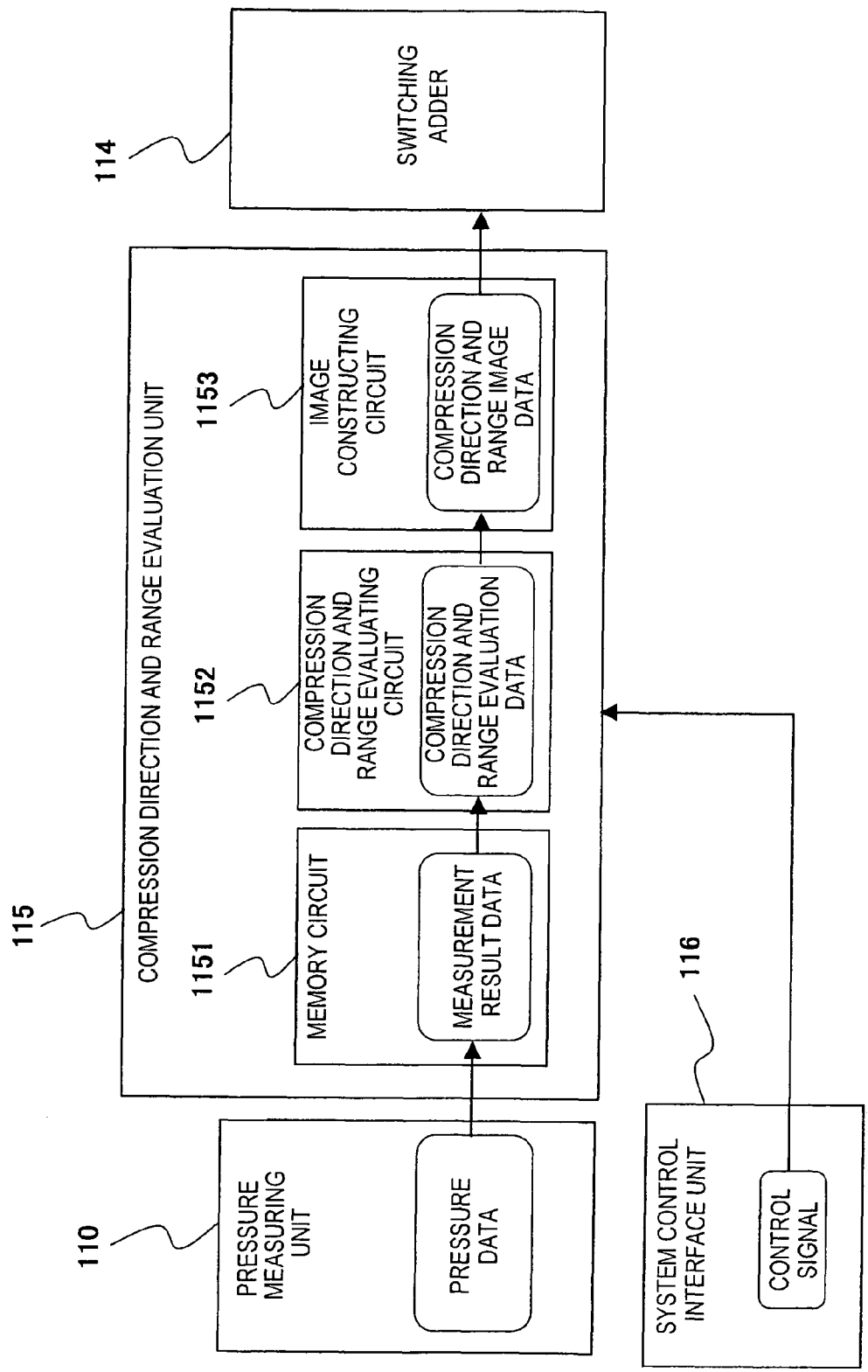
FIG. 15 is a block diagram illustrating an embodiment of a compression direction and range evaluation unit for measuring the compression direction on the basis of pressure data measured by a pressure sensor group.

The compression direction and range evaluation unit 115 may use the pressure data output from the pressure measuring unit 110, instead of the displacement frame data, the elasticity frame data, or the position data. FIG. 14 illustrates the probe 100 of FIG. 2B from the ultrasound transmission and reception surface side. FIG. 15 illustrates the configuration in which the pressure measuring unit 110 is provided on the input side of the compression direction and range evaluation unit 115. As shown in FIG. 14 or 15, the pressure sensor groups 1002 and 1003 detect the pressure for when the ultrasound transmission and reception surface is pressed against the object to be examined. The pressure measuring unit 110 sends the signals output from the pressure sensor groups 1102 and 1003, as pressure data, to the compression direction and range evaluation unit 115. The compression direction and range evaluation unit 115 may measure the compression state of the body tissue on the basis of the pressure data.

Figure 16:
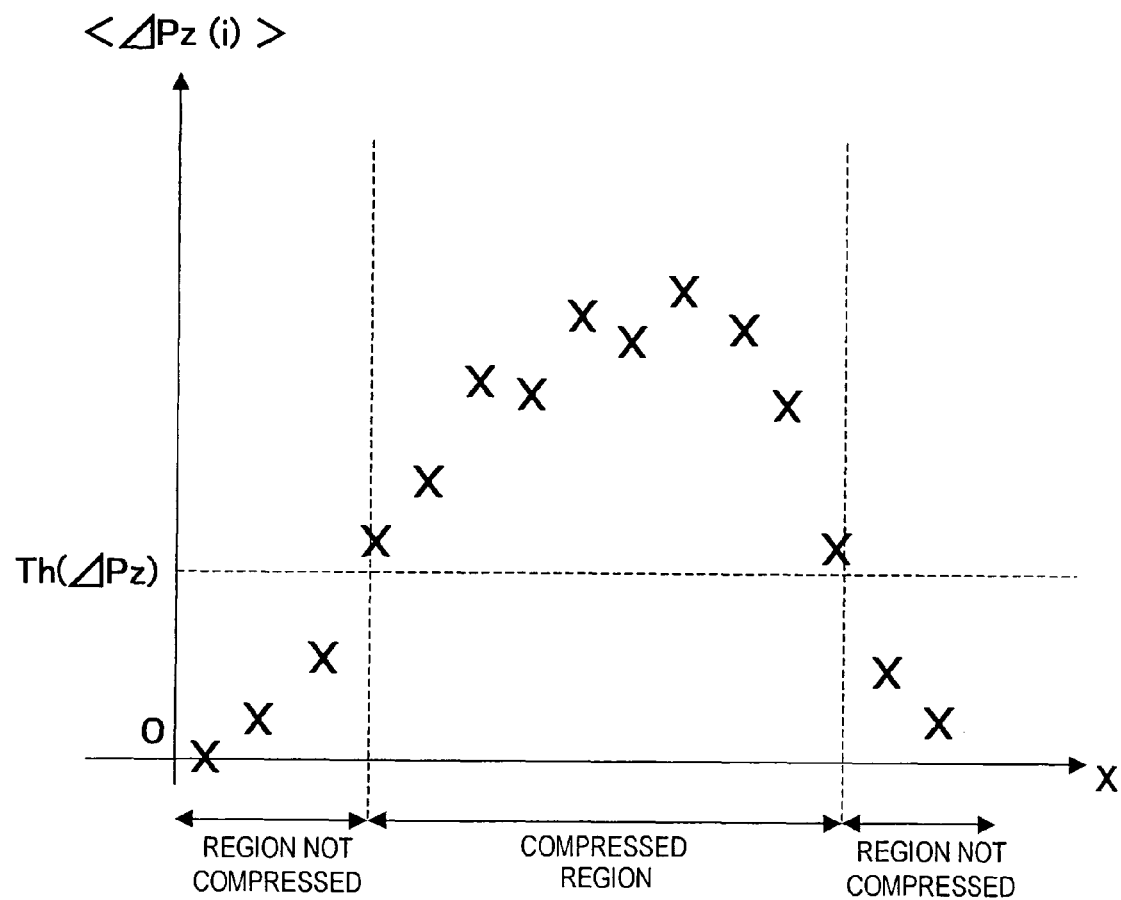
FIG. 16 is a computation example of determining an adequate compression range and an inadequate compression range on the basis of pressure data measured by a pressure sensor group.

For example, the compression direction and range evaluation unit 115 stores pressure data measured in the past in term of time and determines the amount of time variation in the current pressure data and the pressure data of the past output from the pressure measuring unit 110. FIG. 16 is a graph representing the amount of change in the pressure data in the lateral direction X. The longitudinal axis $\Delta Pz(i)$ in FIG. 16 represents the amount of change in the pressure data at the position of each pressure sensor. Index i represents the coordinate in the long axis direction. Index j represents the coordinate in the short axis direction. $<\Delta Pz(i)>$ represents the average value of the pressure data in the short axis direction at each coordinate of the long axis direction and is calculated on the basis Expression 6.

$$<\Delta Pz(i)>=\{<\Delta Pz(i,k)+<\Delta Pz(i,2)\}/2 \qquad \text{(Expression 6)}$$

Next, similar to the case described with referring to FIG. 5 or 11, the compression direction and range evaluation unit 115 sets a threshold value Th($\Delta$Pz) of the amount of pressure change. Then, the compression direction and range evaluation unit 115 determines the lateral direction coordinate region where the amount of pressure change exceeds the threshold value as the current adequate compression range. In contrast, the compression direction and range evaluation unit 115 determines the lateral direction coordinate region where the amount of pressure change is equal to or below the threshold value as the current inadequate compression range.

According to the configuration described with reference to FIGS. 15 and 16, the adequate compression range and the inadequate compression range of the body tissue can be determined more accurately compared with when the displacement frame data or the elasticity frame data is used. For example, the displacement frame data or the elasticity frame data is based on the displacement of the body tissue of when pressure is applied to the object to be examined. Therefore, when the inadequate compression range is determined on the basis of the displacement frame data and the like, it can be presumed that there are cases in which it is difficult to determine whether the range is caused from the hardness of the body tissue or non-uniformity of stress. Thus, by carrying out determination on the basis of the amount of pressure change, an inadequate compression range caused by non-uniformity of stress can be determined more accurately. In other words, the adequate compression range can be determined more accurately.

The compression direction and range evaluation unit 115 may use a value corresponding to the deformation of the reference deforming body 37 shown in FIG. 2B, instead of the displacement frame data, the elasticity frame data, the position data, or the pressure data. For example, deformation detection means detects the deformation of the reference deforming body 37 and estimates the pressure data on the basis of the detected value. The compression direction and range evaluation unit 115 determines the adequate compression range of the body tissue on the basis of the pressure data output from the deformation detection means. In other words, the compression direction and range evaluation unit 115 obtains one of at least the displacement frame data, the elasticity frame data, the position data of the probe 100, the pressure data, and the deformation value of the reference deforming body 37, as compression data, and determines the adequate compression range or the compression direction of the body tissue on the basis of the obtained compression data.

Figure 17:
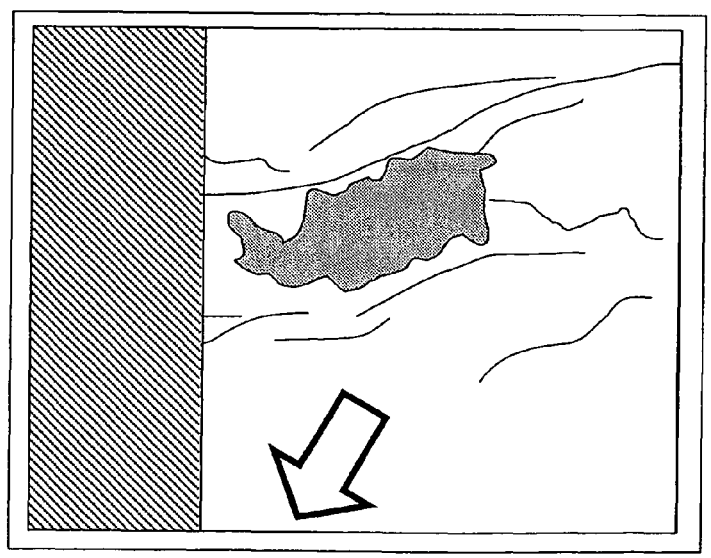
FIG. 17 illustrates a display configuration for when the ultrasound transducer shown in FIG. 2 is used and illustrates a display configuration in which image information of a region corresponding to an inadequate compression range is deleted.
Figure 18:
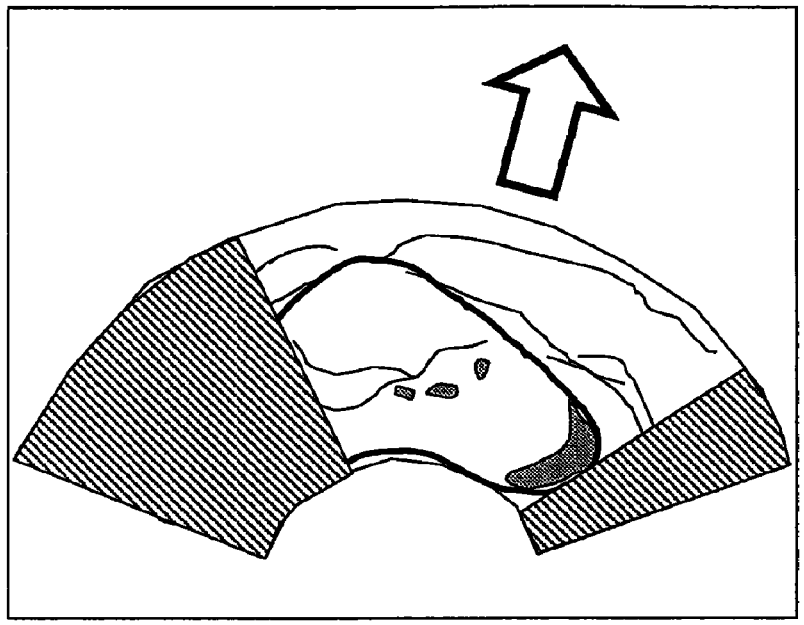
FIG. 18 illustrates a display configuration for when the ultrasound transducer shown in FIG. 8 is used and illustrates a display configuration in which image information of a region corresponding to an inadequate compression range is deleted.

FIG. 17 illustrates another example of the display configuration shown in FIG. 7C. FIG. 18 illustrates another example of a display configuration shown in FIG. 10. The displayed images shown in FIGS. 17 and 18 differ from the display configuration shown in FIG. 7C or 10 in which a black color code is assigned to a predetermined percentage of the pixel points corresponding to the inadequate compression range, in that the cross-sectional image and the elasticity image corresponding to the inadequate compression range are deleted. The processing for deleting images corresponding to the inadequate compression range is carried out by the switching adder 114 in response to a control command. According to such a displayed image, only the images corresponding to the adequate compression range are extracted and displayed. Therefore, the examiner can employ only the adequate compression range as a diagnostic image, and misdiagnosis caused by the inadequate compression range can be reliably prevented.

Figure 19:
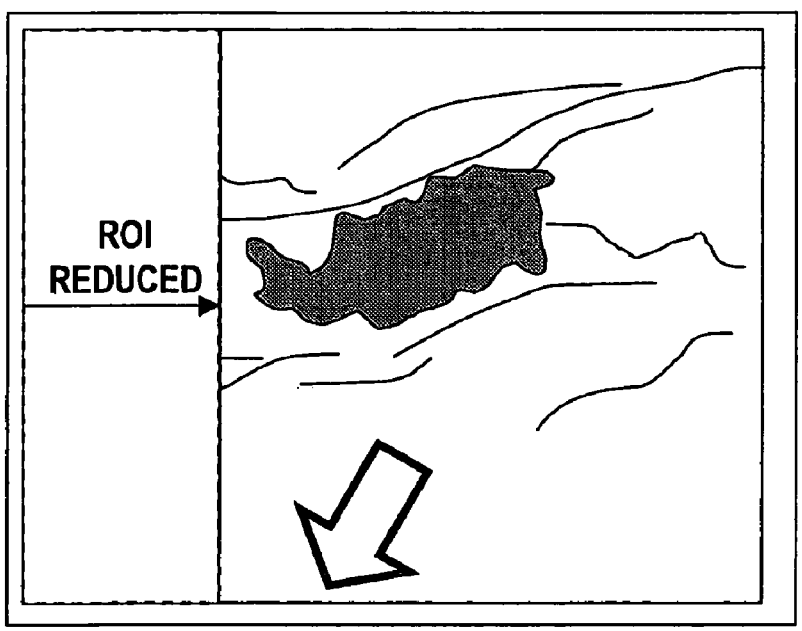
FIG. 19 illustrates a display configuration for when the ultrasound transducer shown in FIG. 2 is used and illustrates a display configuration in which the size of a ROI is changed in accordance with the current compression state.
Figure 20:
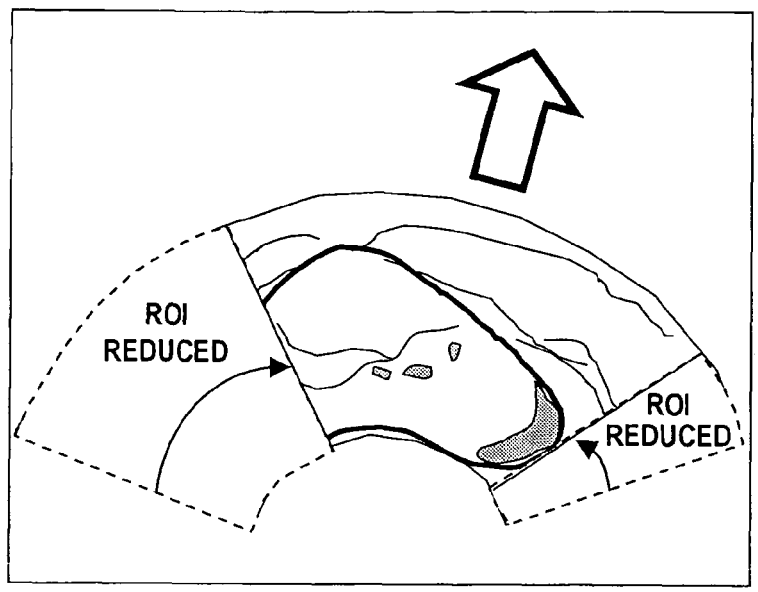
FIG. 20 illustrates a display configuration for when the ultrasound transducer shown in FIG. 8 is used and illustrates a display configuration in which the size of a ROI is changed in accordance with the current compression state.

FIG. 19 illustrates another example of the display configuration shown in FIG. 7C. FIG. 20 illustrates another example of the display configuration shown in FIG. 10. The displayed images shown in FIGS. 19 and 20 differ from the display configuration of FIG. 7C or 10 in which the adequate compression range and the inadequate compression range are included in the region of interest (ROI), in that the an image region corresponding to the adequate compression range is re-set as the region of interest. The re-setting processing of the region of interest is carried out by the switching adder 114 in accordance with a control command. For example, the switching adder 114 carries out processing for changing (for example, reducing) the size of the ROI in real-time in accordance with the current compression state. According to such a displayed image, only images corresponding to the adequate compression range are extracted and displayed. Therefore, the examiner can employ only the adequate compression range as a diagnostic image, and misdiagnosis caused by the inadequate compression range can be reliably prevented. Since the display region is decreased when the ROI is reduced, as shown in this configuration, the processing speed of the displayed image is increased.

Figure 21:
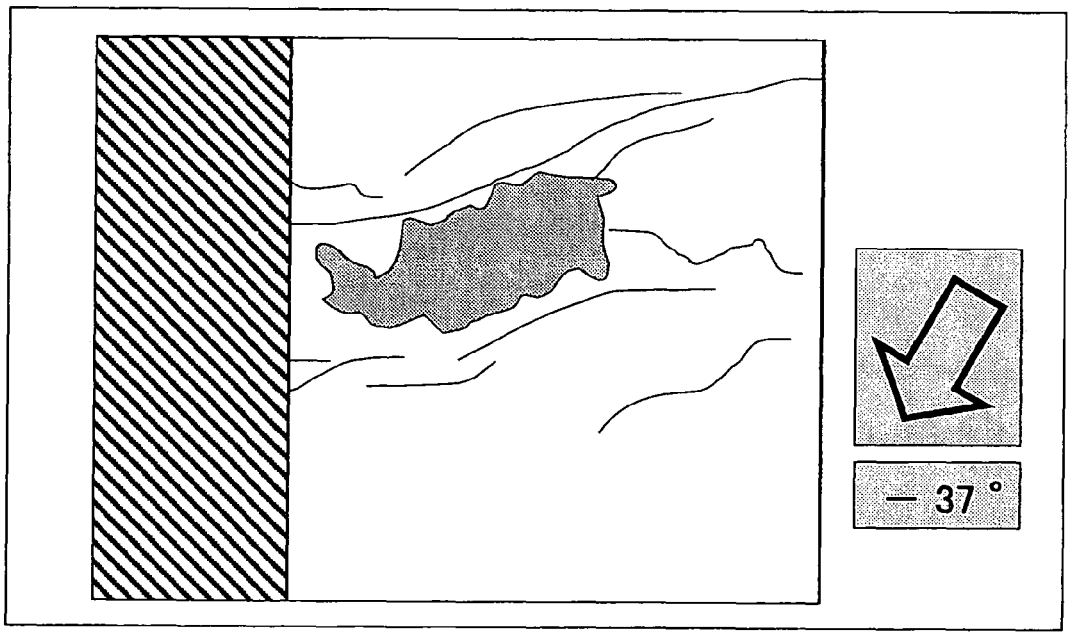
FIG. 21 illustrates a configuration for displaying compression direction image data in a display region set as a separate window.

FIG. 21 illustrates another example of a display configuration shown in FIG. 7C. The display configuration shown in FIG. 21 differs from the display configuration shown in FIG. 7C in which an arrow and a numerical value is displayed in an superimposing manner with the ultrasound image, in that the arrow of the compression direction and the numerical value of the compression angle are displayed adjacently with the ultrasound image. In other words, the display configuration shown in FIG. 21 has a specialized display region as a separate window for displaying the arrow and the compression angle. The processing for defining such a specialized display region is carried out by the switching adder 114. According to this display configuration, the arrow of the compression direction and the numerical value of the compression angle can be easily and visually confirmed.

Figure 22:
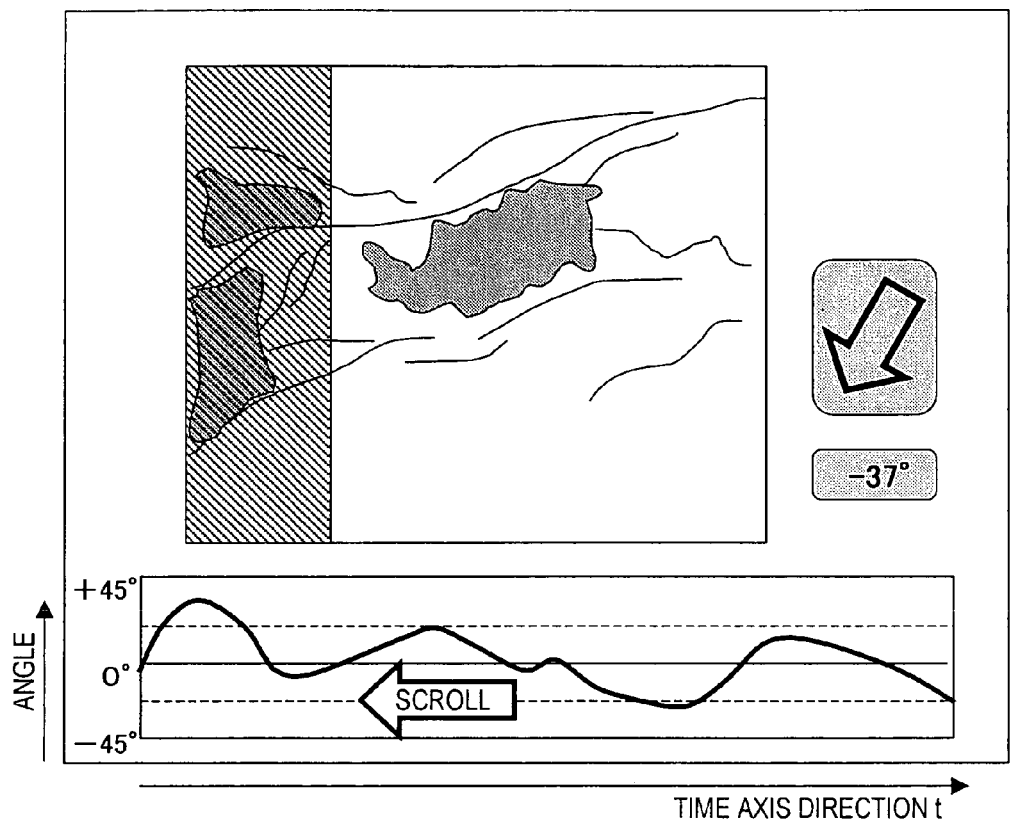
FIG. 22 illustrates a graph representing the time transition of an angle θ representing the compression direction in real-time and illustrates a configuration in which the history of angles θ is scroll-displayed.

FIG. 22 illustrates another example of the display configuration shown in FIG. 7C. The display configuration shown in FIG. 22 differs from the display configuration shown in FIG. 7C in which the current compression angle is displayed, in that the time transition of the compression angle is displayed as a graph. In other words, in the display configuration shown in FIG. 22, a graph display region having a longitudinal axis representing the compression angle and a lateral axis representing the amount of image-capturing time that has elapsed is provided. In the graph display region, the history of the compression angles is time-sequentially displayed in real-time as a graph. Furthermore, the history of compression angles of the past may be scroll-displayed. Such graph display processing is carried out by the switching adder 114. Images obtained by time-sequentially displaying the history of the compression angles in real-time may be referred to as compression direction images. By visually confirming a compression direction image, the time transition of the compression direction can be visually grasped.

Figure 23:
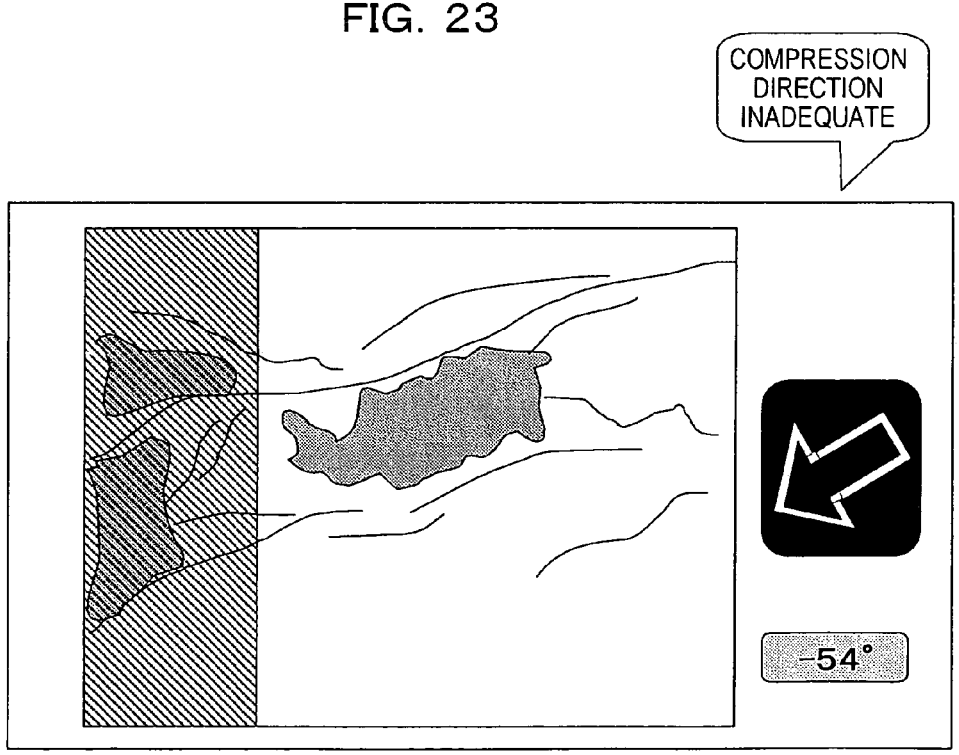
FIG. 23 illustrates a configuration for generating an alert when the compression direction or the compression range is determined to be inadequate.

FIG. 23 illustrates a configuration for generating an alarm in addition to the display configuration shown in FIG. 21. For example, the diagnostic ultrasound system according to this embodiment includes alerting means provided as announcing means for generating an alert of at least one of an image and audio when the compression state evaluation data determined at the compression direction and range evaluation unit 115 is outside the set range. For example, the announcing means determines that the compression direction is inadequate when the angle of the compression direction determined at the compression direction and range evaluation unit 115 exceeds a set value. At this time, the alerting means generates, for example, an audio message, "the compression direction is inadequate," as shown in FIG. 23. Furthermore, the alerting means may flash the arrow indicating the compression direction. The alerting means may change the color of the arrow indicating the compression direction, for example, form white to red. The alerting means may reverse the color of the arrow and the background. In other words, it is acceptable so long as the alerting means generates an alert that can be immediately recognized by the examiner. In this way, since the examiner will be able to quickly correct the compression operation in response to the alert, inadequate compression operation is carried out fewer times, and, thus, the diagnosis efficiency is improved even more. The alerting means may also generate an alert when the compression range is inadequate.

As described above, according to this embodiment, a diagnostic ultrasound system and a method of displaying an elasticity image that enables accurate diagnosis by objectively and quantitatively grasping the compression condition of body tissue are provided. In other words, according to prior methods, non-uniformity in the stress distribution of body tissue is generated because both an adequate compression range and an inadequate compression range exist in the body tissue corresponding to the display range of an elasticity image. In such a case, since sometimes the inadequate compression range is displayed as a hard region, there is a possibility of diagnosing the tissue in the inadequate compression range as being false-positive. In this regard, according to this embodiment, an adequate compression range and a compression direction of body tissue can be estimated or detected at a predetermined point of time in real-time, and the adequate compression range and the compression direction can be reflected on an elasticity image. By visualizing the adequate compression range and the compression direction and providing them to the examiner as feedback, the examiner can objectively and quantitatively recognize the adequate compression range and the compression direction on the image. Therefore, the examiner can avoid the possibility of misdiagnosing the inadequate compression range as being positive. Moreover, regardless of the differences in the compression operation that depends on the procedures carried out by each examiner, an image diagnosis with assured objectivity and reproducibility becomes possible.

In essence, according to this embodiment, an elasticity image obtained under predetermined compression conditions is extracted on the basis of an objective criterion so as to efficiently carry out objective image diagnosis that does not rely on the examiner's object to be examinedivity. In other words, by providing an elasticity image that is simultaneously stored with information on the compression state, highly objective elasticity image diagnosis becomes possible. In this way, according to this embodiment, a clinically useful diagnostic ultrasound system can be provided.

As described with reference to FIGS. 1 to 23, the method of displaying an elasticity image according to this embodiment includes a transmission and reception step of processing a reception signal output from the probe 100 after supplying a driving signal for transmission to the probe 100 that alternately converts ultrasonic waves and electrical signals; a determination step of obtaining compression data related to the compression state of body tissue of the object to be examined 10 on the basis of the reception signal output in the transmission and reception step and determining the adequate compression range or the compression direction of the body tissue on the basis of the compression data; and a display step of displaying an image reflecting the determination result to an elasticity image.

Here, a method of displaying an image by using the cine memory unit 117 according to this embodiment will be described. The cine memory unit 117, shown in FIG. 1, has functions of storing display image data output from the switching adder 114 in a memory, reading out current or past image data from the memory in response to a command from the system control interface unit 116, and outputting the image data to the image display unit 107. Furthermore, the cine memory unit 117 has a function of transferring the image data read out from the memory to a storage medium, such as an MO. Furthermore, the cine memory unit 117 has a function of carrying out processing for reading out image data or extracting optimal compression direction and range on the basis of the compression state evaluation data output from the compression direction and range evaluation unit 115.

Figure 24:
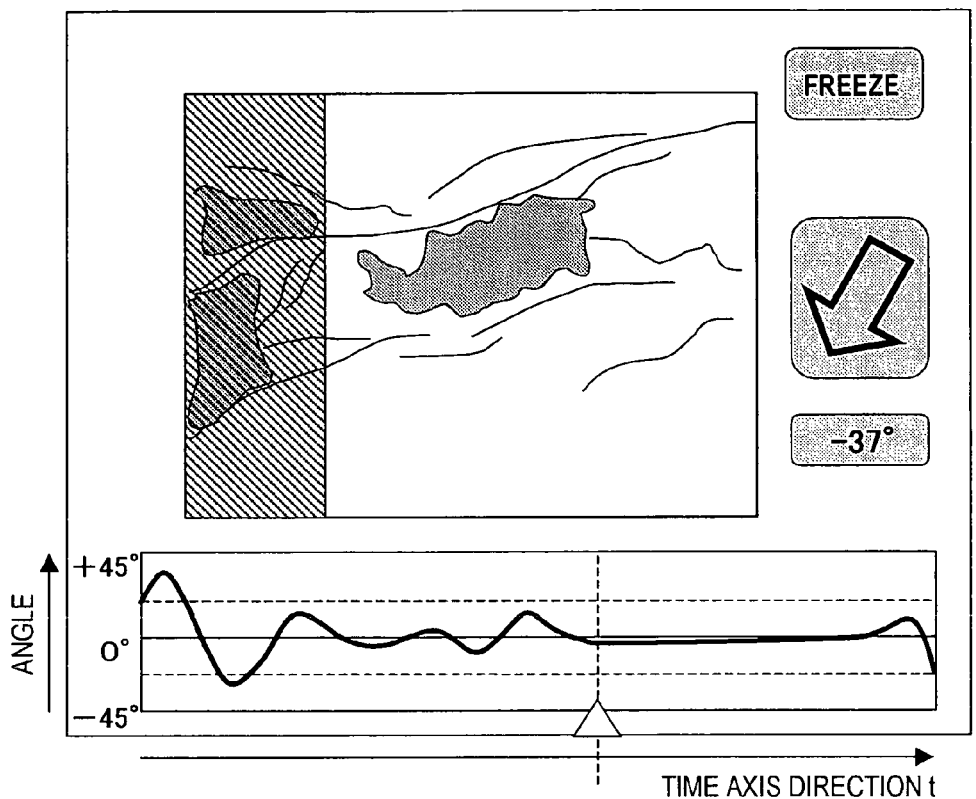
FIG. 24 illustrates a configuration for displaying image data corresponding to an assigned point of time.

FIG. 24 illustrates a display configuration for describing the operation of the cine memory unit 117. In this example, a point of time for image-capturing is assigned on the compression direction image shown in FIG. 22, and the image data of the assigned point of time is read out and displayed. For example, in response to a command of the system control interface unit 116, the diagnostic ultrasound system is frozen. The examiner assigns a predetermined point of time for image-capturing on the compression direction image by moving a graphical user interface (for example, an arrow), shown in FIG. 24, via the system control interface unit 116. The cine memory unit 117 reads out image data corresponding to the assigned point of time and displays the read out image data on the image display unit 107 as an ultrasound diagnosis image. The image data group stored in the cine memory unit 117 is related to the compression direction image on the same time axis. Here, the compression direction image is a time-sequential image of the history of the compression angles displayed in real-time. According to the configuration shown in FIG. 24, since an elasticity image for when the compression direction is adequate can be quickly and accurately displayed, the diagnosis accuracy and the diagnosis efficiency are improved.

Figure 25:
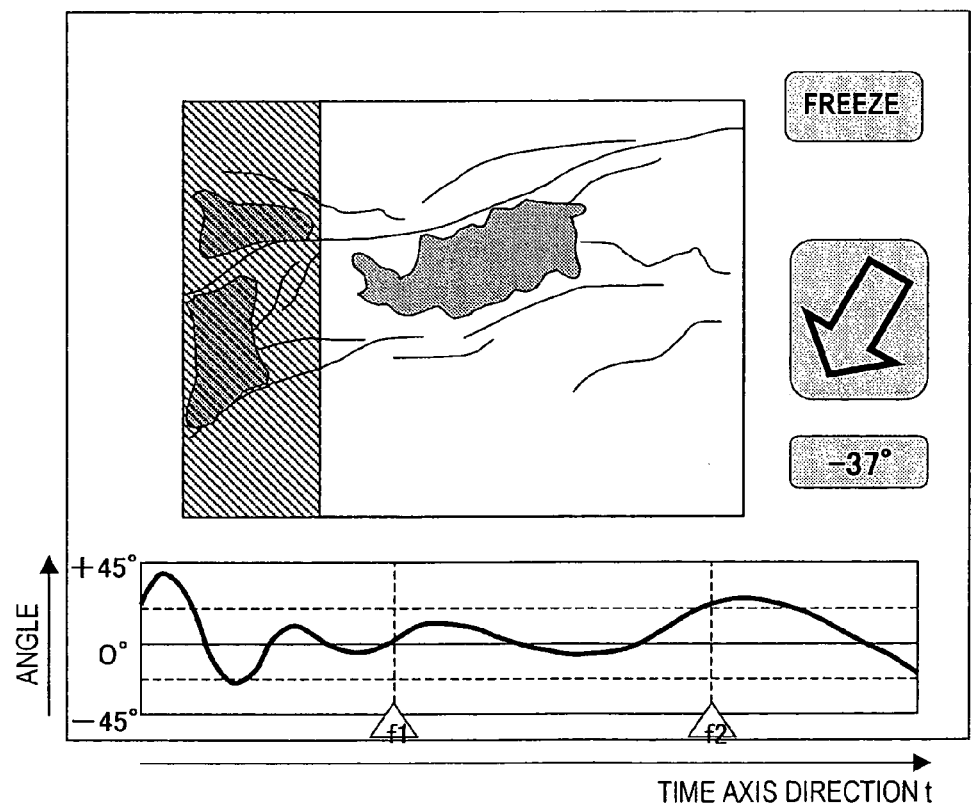
FIG. 25 illustrates a configuration for displaying in order the first image data to the last image data corresponding to an assigned period.

FIG. 25 illustrates a display configuration for describing another operation of the cine memory unit 117. This example differs from the configuration shown in FIG. 24 in which one point of time for image-capturing is assigned, in that two points of time for image-capturing are assigned on the compression direction image and an image data group for between the first point of time for image-capturing and the second point of time for image-capturing is displayed in order. For example, the examiner assigns two points of time for image-capturing on the compression direction image by moving a graphical user interface (for example, two arrows), shown in FIG. 25, via the system control interface unit 116. The cine memory unit 117 reads out, in order, image data (f1) corresponding to the first assigned point of time to the image data (f2) corresponding to the last assigned point of time from the memory. Then, the cine memory unit 117 displays the time-sequential image data read out from the memory as ultrasound diagnosis image on the image display unit 107. According to the configuration shown in FIG. 25, since time-sequential images for when the compression direction is adequate can be quickly and accurately displayed, the diagnosis accuracy and the diagnosis efficiency are improved when diagnosing body tissue with body motion.

Figure 26:
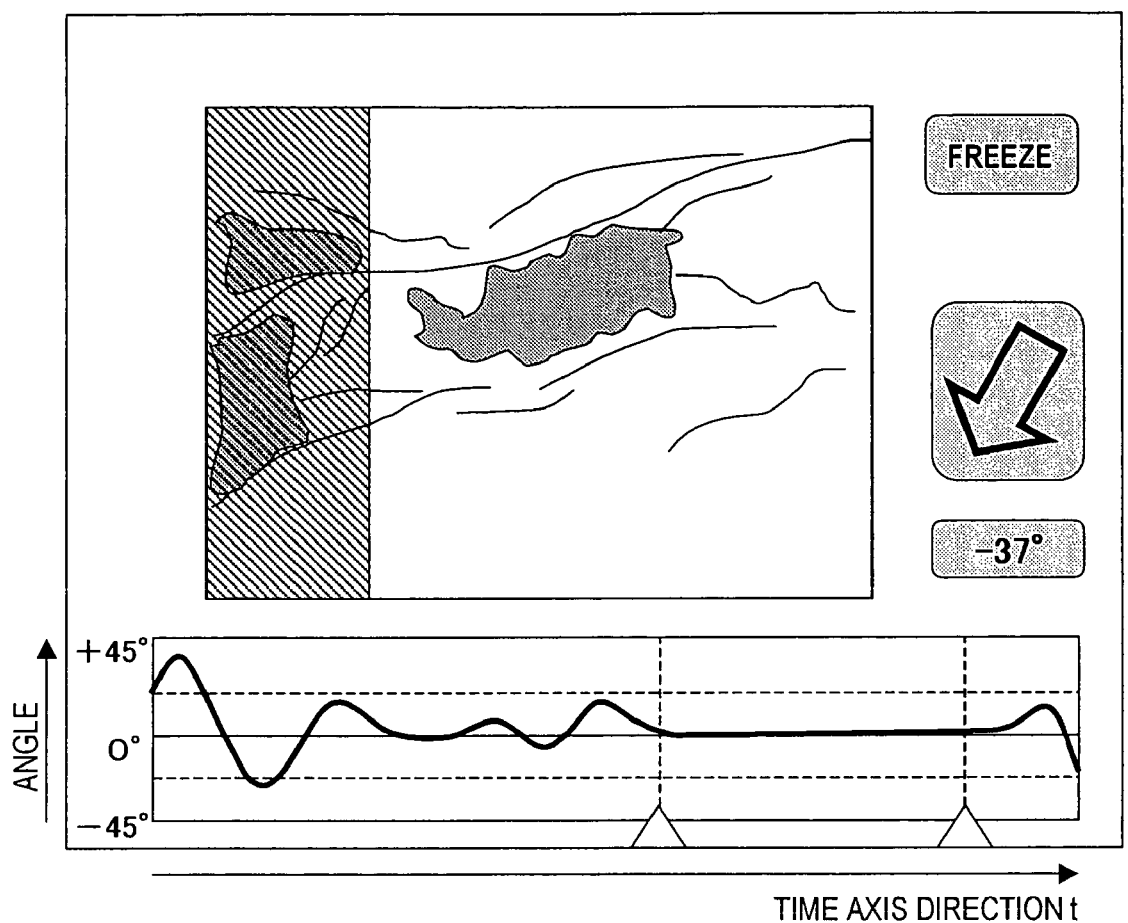
FIG. 26 illustrates a configuration for displaying image data for when the compression direction is included in a set range with reference to zero.

FIG. 26 illustrates a display configuration for describing another operation of the cine memory unit 117. This example differs from the configurations shown in FIGS. 24 and 25 in that an image data group for when compression is carried out in an adequate compression direction is automatically detected and displayed. For example, the cine memory unit 117 automatically detects the first and last points of time for image-capturing of the period in which adequate compression is carried out on the basis of the compression angle output from the compression direction and range evaluation unit 115, extracts an image data group corresponding to the detected period, and displays the image data group on the image display unit 107. More specifically, as shown in FIG. 26, the cine memory unit 117 automatically detects the image-capturing period in which the compression angle output from the compression direction and range evaluation unit 115 belongs to a set range with reference to zero. In other words, the cine memory unit 117 automatically detects an image-capturing period for, for example, when the compression angle is substantially orthogonal to the body surface of the object to be examined. Then, the cine memory unit 117 reads out an image data group corresponding to the period between the first point of time and the last point of time in the detected period and displays this on the image display unit 107. According to the configuration shown in FIG. 26, regardless of the differences in the examiners' experience, since an adequate image-capturing period is set, the diagnosis accuracy and the diagnosis efficiency are improved.

The operation of the cine memory unit 117 has been described with reference to FIGS. 24 to 26. However, instead of using a compression direction image when displaying an ultrasound diagnosis image, the values of the compression state evaluation data (for example, the adequate compression range and the compression direction) output from the compression direction and range evaluation unit 115 may be used. In the configuration shown in FIGS. 24 to 26, the cine memory unit 117 can consecutively playback an image data group that is read out from the memory in a repeated loop and display it on the image display unit 107 in accordance with a command of the system control interface unit 116. The cine memory unit 117 can transfer and store the image data group read out from the memory to and on a storage medium, such as an MO. The storage medium is internally or externally installed to the diagnostic ultrasound system.

The functions of the diagnostic ultrasound system according to this embodiment may be switched appropriately on the basis of commands output from the system control interface unit 116. For example, the examiner can freely select, with the system control interface unit 116, one set or a plurality of sets of information constituting image data representing the compression direction and range among the information representing the compression state (for example, the compression direction, the compression angle, and the compression range). Furthermore, the examiner can freely control, with the system control interface unit 116, the selection of whether or not to display compression direction and range image data and the setting of the display angle range for a compression direction image and the time range of the compression angle history.

In the above, embodiments of a diagnostic ultrasound system employing the present invention was described. However, the diagnostic ultrasound system is not limited to the embodiments. The diagnostic ultrasound system according to the present invention can be employ various other configurations without deviating from the scope and the essential characteristics of the present invention. Therefore, the above-described embodiments are merely examples and are not to be understood as limitations. The scope of the present invention includes modifications and variations that belong to an equivalent scope.

As described above, according to this embodiment, a diagnostic ultrasound system and a method of displaying an elasticity image that enables a more accurate diagnosis by objectively and quantitatively grasping the compression state of body tissue can be provided.

The invention claimed is:

1. A diagnostic ultrasound system comprising:
an ultrasound transducer for transmitting and receiving ultrasound waves to and from an object to be examined;
transmitting means for supplying a driving signal to the ultrasound transducer;
receiving means for processing a reception signal output from the ultrasound transducer;
elasticity image imaging means for obtaining an elasticity image related to a body tissue of the object to be examined on the basis of a signal output from the receiving means; and
displaying means for displaying the elasticity image,
wherein the elasticity image imaging means includes compression state evaluating means for:
obtaining compression data related to a compression state of the body tissue of the object to be examined, and
determining that: a coordinate region with a magnitude of the compression data exceeding a threshold value is within an adequate compression range; and a coordinate region with a magnitude of the compression data not exceeding the threshold value is an inadequate compression range, wherein
at least one of the adequate compression ranges and at least one of the inadequate compression ranges are displayed on the elasticity image, with a border between the adequate compression range and the inadequate compression range.

2. A diagnostic ultrasound system comprising:
an ultrasound transducer for transmitting and receiving ultrasonic waves to and from an object to be examined;
transmitting means for supplying a driving signal to the ultrasound transducer;
receiving means for processing a reception signal output from the ultrasound transducer;
elasticity image imaging means for obtaining an elasticity image related to a body tissue of the object to be examined on the basis of a signal output from the receiving means; and
displaying means for displaying the elasticity image,
wherein the elasticity image imaging means includes compression state evaluating means for:
obtaining compression data related to a compression state of the body tissue of the object to be examined,
determining that: a coordinate region with a magnitude of the compression data exceeding a threshold value is within an adequate compression range; and a coordinate region with a magnitude of the compression data not exceeding the threshold value is an inadequate compression range, wherein at least one of the adequate compression ranges and at least one of the inadequate compression ranges are displayed on the elasticity image, with a border between the adequate compression range and the inadequate compression range,
determining a compression direction of the body tissue on the basis of a distribution of magnitude of the compression data, and
reflecting the compression direction on the elasticity image,
wherein the compression direction is represented by an angle of compression.

3. The diagnostic ultrasound system according to claim 1, wherein the compression state evaluating means obtains elasticity data related to the body tissue and determined at the elasticity image imaging means as the compression data.

4. The diagnostic ultrasound system according to claim 1, wherein the compression state evaluating means obtains detection values of a plurality of pressure sensors aligned on an ultrasound transmission and reception surface of the ultrasound transducer as the compression data.

5. The diagnostic ultrasound system according to claim 4, wherein a plurality of the pressure sensors are aligned in a long axis direction of the ultrasound transmission and reception surface.

6. The diagnostic ultrasound system according to claim 4, wherein the pressure sensors comprise a reference deforming body deformable by compression.

7. The diagnostic ultrasound system according to claim 1, wherein the compression state evaluating means obtains a deformation value of a reference deforming body stacked on the ultrasound transmission and reception surface of the ultrasound transducer as the compression data.

8. The diagnostic ultrasound system according to claim 1, wherein the compression state evaluating means obtains a detection value of a position sensor attached to the ultrasound transducer as the compression data.

9. The diagnostic ultrasound system according to claim 1, wherein the compression state evaluating means separates elasticity data of measurement points of the body tissue determined at the elasticity image imaging means into displacement vector components of a longitudinal direction corresponding to a depth direction of the object to be examined and displacement vector components of a lateral direction orthogonal to the depth direction, and determines the adequate compression range by comparing the magnitude of the displacement vector components of the longitudinal direction or the magnitude of the displacement vector components of the lateral direction with a set value.

10. The diagnostic ultrasound system according to claim 2, wherein the compression state evaluating means separates elasticity data of measurement points of the body tissue determined at the elasticity image imaging means into displacement vector components of a longitudinal direction corresponding to a depth direction of the object to be examined and displacement vector components of a lateral direction orthogonal to the depth direction, and determines the compression direction on the basis of the distribution of the magnitude of the displacement vector components of the longitudinal direction or the distribution of the magnitude of the displacement vector components of the lateral direction.

11. The diagnostic ultrasound system according to claim 1, wherein the compression state evaluating means generates image data representing the adequate compression range, and the displaying means displays the image data in a superimposing manner on or adjacent to the elasticity image.

12. The diagnostic ultrasound system according to claim 2, wherein the compression state evaluating means generates image data or numerical data representing the compression direction, and the displaying means displays the image data or the numerical data in a superimposing manner on or adjacent to the elasticity image.

13. The diagnostic ultrasound system according to claim 1, wherein the compression state evaluating means generates image data representing the border of the adequate compression range and the inadequate compression range, and the displaying means displays the image data in a superimposing manner on or adjacent to the elasticity image.

14. The diagnostic ultrasound system according to claim 1, wherein the displaying means displays a region of interest whose size is changed on the basis of a determination result of the compression state evaluating means.

15. The diagnostic ultrasound system according to claim 1, wherein the compression state evaluating means repeatedly determines the adequate compression range in set intervals, and the displaying means updates and displays image data representing the adequate compression range in real-time every time the determination result is updated.

16. The diagnostic ultrasound system according to claim 2, wherein the compression state evaluating means repeatedly determines the compression direction in set intervals, and the displaying means updates and displays image data or numerical data representing the compression direction in real-time every time the determination result is updated.

17. The diagnostic ultrasound system according to claim 2, wherein the compression state evaluating means generates image data of an arrow indicating the compression direction or numerical data representing the angle corresponding to the compression direction, and the displaying means displays an image corresponding to the image data or the numerical data in a superimposing manner on or adjacent to the elasticity image.

18. The diagnostic ultrasound system according to claim 2, wherein the compression state evaluating means repeatedly determines the compression direction in set intervals, and the displaying means displays the time transition of the angle representing the compression direction on the basis of the determination result.

19. The diagnostic ultrasound system according to claim 1, further comprising:
a cine memory for exacting and reading out at least one of the elasticity image stored in advance and image data or numerical data corresponding to the compression state on the basis of compression state evaluation data output from the compression state evaluating means.

20. The diagnostic ultrasound system according to claim 2, wherein the compression state evaluating means repeatedly determines the compression direction in set intervals, and the displaying means displays the elasticity image for when the angle representing the compression direction is included in a set range with reference to zero.

21. The diagnostic ultrasound system according to claim 2, wherein the compression state evaluating means repeatedly determines the compression direction in set intervals, and the displaying means time-sequentially displays the elasticity image group for when the angle representing the compression direction is included in a set range with reference to zero.

22. The diagnostic ultrasound system according to claim 1, wherein the compression state evaluating means includes announcing means for generating an alert of at least one of an image and audio when the adequate compression range corresponding to outside a set range.

23. The diagnostic ultrasound system according to claim 2, wherein the compression state evaluating means includes announcing means for generating an alert of at least one of an image and audio when the compression direction corresponding to outside a set range.

24. The diagnostic ultrasound system according to claim 2, wherein the compression state evaluating means obtains elasticity data related to the body tissue and determined at the elasticity image imaging means as the compression data.

25. The diagnostic ultrasound system according to claim 2, wherein the compression state evaluating means obtains detection values of a plurality of pressure sensors aligned on an ultrasound transmission and reception surface of the ultrasound transducer as the compression data.

26. The diagnostic ultrasound system according to claim 2, wherein the compression state evaluating means obtains a deformation value of a reference deforming body stacked on the ultrasound transmission and reception surface of the ultrasound transducer as the compression data.

27. The diagnostic ultrasound system according to claim 2, wherein the compression state evaluating means obtains a detection value of a position sensor attached to the ultrasound transducer as the compression data.

28. The diagnostic ultrasound system according to claim 2, further comprising:
a cine memory for exacting and reading out at least one of the elasticity image stored in advance and image data or numerical data corresponding to the compression state on the basis of compression state evaluation data output from the compression state evaluating means.

* * * * *